(12) United States Patent
Hu et al.

(10) Patent No.: US 8,470,842 B2
(45) Date of Patent: Jun. 25, 2013

(54) HYDROCHLORIDE SALTS OF 8-[{1-(3,5-BIS-TRIFLUOROMETHYL) PHENYL)-ETHOXY}-METHYL]-8-PHENYL-1,7-DIAZA-SPIRO[4.5]DECAN-2-ONE AND PREPARATION PROCESS THEREFOR

(75) Inventors: Mengwei Hu, Washington, NJ (US); Sunil Paliwal, Monroe Township, NJ (US); Neng-Yang Shih, Lexington, MA (US); Frank Bruno Guenter, Schachen (CH); Ingrid Mergelsberg, Mahwah, NJ (US)

(73) Assignee: OPKO Health, Inc., Miami, FL (US)

( * ) Notice: Subject to any disclaimer, the term of this patent is extended or adjusted under 35 U.S.C. 154(b) by 565 days.

(21) Appl. No.: 12/614,108

(22) Filed: Nov. 6, 2009

(65) Prior Publication Data

US 2010/0048601 A1 Feb. 25, 2010

Related U.S. Application Data

(63) Continuation of application No. 11/732,548, filed on Apr. 4, 2007, now Pat. No. 8,178,550.

(60) Provisional application No. 60/789,280, filed on Apr. 5, 2006.

(51) Int. Cl.
*A01N 43/42* (2006.01)
*A61K 31/44* (2006.01)
*C07D 215/00* (2006.01)
*C07D 217/00* (2006.01)
*C07D 219/00* (2006.01)
*C07D 221/00* (2006.01)

(52) U.S. Cl.
USPC .......................................... 514/278; 546/16

(58) Field of Classification Search
None
See application file for complete search history.

(56) References Cited

U.S. PATENT DOCUMENTS

| | | |
|---|---|---|
| 7,049,320 B2 | 5/2006 | Paliwal et al. |
| 7,183,272 B2 | 2/2007 | Aronhime et al. |
| 7,323,459 B2 | 1/2008 | Dolitzky et al. |
| 7,534,913 B2 | 5/2009 | Frenkel et al. |
| 7,563,801 B2 | 7/2009 | Qiu et al. |
| 7,709,641 B2 | 5/2010 | Shah et al. |
| 7,879,867 B2 | 2/2011 | Paredes et al. |
| 7,897,613 B2 | 3/2011 | Arul et al. |
| 7,902,366 B2 | 3/2011 | Paliwal et al. |
| 7,981,905 B2 | 7/2011 | Qiu et al. |
| 8,178,550 B2 | 5/2012 | Hu et al. |
| 2003/0158173 A1 | 8/2003 | Paliwal et al. |
| 2010/0087426 A1 | 4/2010 | Mergelsberg et al. |
| 2010/0104637 A1 | 4/2010 | Qiu et al. |
| 2011/0038925 A1 | 2/2011 | Wan et al. |
| 2011/0098468 A1 | 4/2011 | Paliwal et al. |
| 2012/0015921 A1 | 1/2012 | Qiu et al. |

FOREIGN PATENT DOCUMENTS

| | | |
|---|---|---|
| WO | WO-2005/063243 A1 | 7/2005 |
| WO | WO-2007117486 A2 | 10/2007 |
| WO | WO-2010028232 A1 | 3/2010 |

OTHER PUBLICATIONS

Sarna et al. Gastroenterol. Clin. North Am. Jun. 1989, 18(2), pp. 375-404 (abstract).*
Berge et al. Pharmaceutical Salts, Review Article, Journal of Pharmaceutical Sciences, (1997).
Brittain et al. Polymorphism in Pharmaceutical Dosage Forms, Polymorphism in Pharmaceutical Solids XX, 235-238 (1999).
Brittain et al. Polymorphism in Pharmaceutical Dosage Forms, Polymorphism in Pharmaceutical Solids XX, 348-361, see p. 357, second full paragraph (1999).
Brittain, Methods for the Characterization of Polymorphs and Solvates, Polymorphism in Pharmaceutical Solids, vol. 95, Chapter 6:227-278 (1999).
Brittain, Spectral Methods for the Characterization of Polymorphs and Solvates, Journal of Pharmaceutical Sciences, vol. 86(4) (1997).
Database Prousddr; Prous Science; Provenza 388; May 9, 2004 ; 1 page.
Geselbracht, Reed College, Introduction to X-ray Powder Diffraction, posted on VIPEr on Feb. 22, 2008.
International Search Report for PCT/US2007/008344 (WO 2007/117486), mailed on Oct. 25, 2007.
Morissette et al., High-throughput crystallization: polymorphs, salts, co-crystals and solvates of pharmaceutical solids, Advanced Drug Delivery Reviews 56:275-300 (2004).
Otsuka et al., Comparative Determination of Polymorphs of Indomethacin in Powders and Tablets by Chemometrical Near-Infrared Spectroscopy and X-ray Powder Diffractometry, AAPS PharmSciTech, 4(2), Article 19:1-12 (2003).
Vippagunta et al. Crystalline solids, Advanced Drug Delivery Reviews, 48:3-26 (2001).

* cited by examiner

*Primary Examiner* — Anna Pagonakis
(74) *Attorney, Agent, or Firm* — Choate, Hall & Stewart LLP; Brenda Herschbach Jarrell; Kristen C. Buteau

(57) ABSTRACT

Disclosed are hydrochloride and tosylate crystalline salt forms of (5S,8S)-8-[{(1R)-1-(3,5-Bis-(trifluoromethyl)phenyl)-ethoxy}-methyl]-8-phenyl-1,7-diazaspiro[4.5]decan-2-one, represented by Formula I and methods of preparing the same.

16 Claims, 22 Drawing Sheets

HYDROCHLORIDE SALTS OF 8-[{1-(3,5-BIS-TRIFLUOROMETHYL) PHENYL)-ETHOXY}-METHYL]-8-PHENYL-1,7-DIAZA-SPIRO[4.5]DECAN-2-ONE AND PREPARATION PROCESS THEREFOR

CROSS REFERENCE TO RELATED APPLICATIONS

This application claims benefit of priority to U.S. application Ser. No. 11/732,548, filed Apr. 4, 2007, which application in turn claims the priority of U.S. Provisional Patent Application Ser. No. 60/789,280, filed Apr. 5, 2006, each of which application is incorporated by reference in its entirety as if fully set forth herein.

FIELD OF THE INVENTION

This patent application generally relates to pharmaceutically useful salts and a novel process to prepare pharmaceutically useful salts. It specifically relates to a novel process to synthesize pharmaceutically useful salts of 8-[{1-(3,5-Bis-(trifluoromethyl)phenyl)-ethoxy}-methyl]-8-phenyl-1,7-diaza-spiro[4.5]decan-2-one.

BACKGROUND OF THE INVENTION

The preparation of diazaspirodecan-2-ones, in particular, 8-[{1-(3,5-Bis-(trifluoromethyl)phenyl)-ethoxy}-methyl]-8-phenyl-1,7-diaza-spiro[4.5]decan-2-ones, for example, (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) is disclosed in U.S. Pat. No. 7,049,320, issued May 23, 2006 (the '320 patent) which is incorporated herein by reference in its entirety.

Formula I

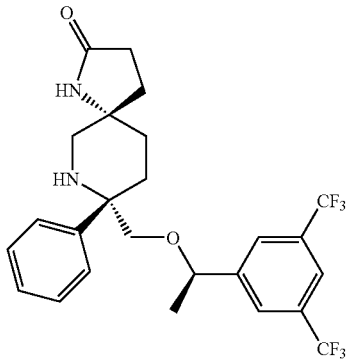

The novel compounds disclosed in the '320 patent are classified as Tachykinin compounds, and are antagonists of neuropeptide neurokinin-1 receptors (referred to herein for convenience as "NK-1 receptor antagonists").

The compounds described in the '320 patent are classified as tachykinin compounds, and are antagonists of neuropeptide neurokinin-1 receptors (herein, "NK-1" receptor antagonists). Other $NK_1$ receptor antagonists and their synthesis have been described, for example, those described in Wu et al, *Tetrahedron* 56, 3043-3051 (2000); Rombouts et al, *Tetrahedron Letters* 42, 7397-7399 (2001); Rogiers et al, *Tetrahedron* 57, 8971-8981 (2001) and in each of the following publications: published international application no. WO05/100358; U.S. Pat. No. 5,760,018 (1998); U.S. Pat. No. 5,620,989 (1997), and international publication nos. WO 95/19344 (1995), WO 94/13639 (1994), and WO 94/10165 (1994), each of which are incorporated herein in their entirety by reference.

"NK-1" receptor antagonists have been shown to be useful therapeutic agents, for example, in the treatment of pain, inflammation, migraine, emesis (vomiting), and nociception. The novel NK-1 compounds disclosed in the above-mentioned '320 patent include the compound of Formula I, which is useful in the treatment of nausea and emesis associated with chemotherapy treatments (Chemotherapy-induced nausea and emesis, CINE). Emesis and nausea have been a problem in the provision of chemotherapy. Chemotherapeutic agents, for example, cisplatin carboplatin and temozolomide have been associated with both acute and delayed onset nausea and vomiting. It is known to administer chemotherapeutic agents with an anti-emetic, for example, as described in U.S. Pat. No. 5,939,098, which describes coadministration of temozolomide and with ondansetron, however such therapy is not effective in preventing delayed onset nausea and vomiting.

As reported in the '320 patent, the compound of Formula I was characterized by TLC and by GC/MS techniques. The procedures described in the '320 patent yielded the compound of Formula I in the form of an amorphous white foam. Repeated attempts to crystallize the free base have not provided a crystalline material.

In general, compounds which have been identified as having therapeutic activity must be provided in a highly pure form for pharmaceutical use. Moreover, it is desirable to provide compounds intended for pharmaceutical use in a form such that it is handled easily for incorporation into a medicament, and when incorporated into a medicament the compound possesses a sufficiently robust character that it is resistant to chemical degradation, and thereby imparts a long shelf life to the medicament.

OBJECTIVES AND SUMMARY OF THE INVENTION

In view of the foregoing, what is desired is a form of the therapeutic agent which lends itself to providing the therapeutic agent in a highly purified form. What is desired also is a form of the therapeutic agent which is robust toward degradation under the environmental conditions in which it is handled and stored.

These and other objectives are advantageously provided by the present invention, which in one aspect provides the compound of Formula I in a salt form which is crystalline and optionally incorporates one or more solvent molecules thereinto, for example, a crystalline monohydrate. In some embodiments it is preferred to select the salt form of compound I from a hydrochloride salt and a Tosylate salt, more preferably, a hydrochloride monohydrate salt form of the compound of Formula I.

Another aspect of the present invention is the provision of a crystalline hydrochloride monohydrate salt form of (5S, 8S)-8-[{(1R)-1-(3,5-Bis-(trifluoromethyl)phenyl)-ethoxy}-methyl]-8-phenyl-1,7-diazaspiro[4.5]decan-2-one (the hydrochloride monohydrate compound of Formula II)

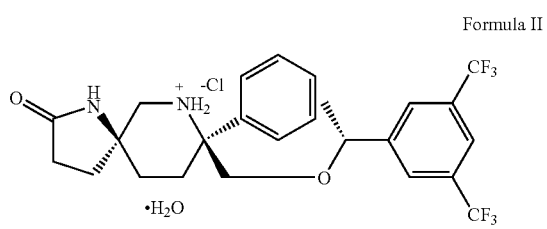

Formula II which is characterized by the x-ray powder diffraction pattern shown in Table I expressed in terms of diffraction angle (in 2θ, all values reflect an accuracy of ±0.2) lattice "d" spacing (in angstroms) and relative peak intensities ("RI"):

TABLE I

| Diffraction angle (2θ, ±0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78 |

Another aspect of the present invention is the provision of a crystalline hydrochloride anhydrous salt form (HCl Anhydrous Form I) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table II expressed in terms of diffraction angle (in 2θ), lattice "d" spacing (in angstroms) and relative peak intensities ("RI"):

TABLE II

| Diffraction angle (2θ, ±0.2) | RI | Lattice Spacing (Å ± 0.04) |
|---|---|---|
| 12.9 | Strong | 6.86 |
| 15.4 | Strong | 5.75 |
| 17.3 | Strong | 5.13 |
| 20.2 | Strong | 4.39 |

Another aspect of the present invention is the provision of a crystalline hydrochloride anhydrous salt form (HCl Anhydrous Form II) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table III expressed in terms of diffraction angle (in 2θ), lattice "d" spacing (in angstroms) and relative peak intensities ("RI"):

TABLE III

| Diffraction angle (2θ, ±0.2) | RI | Lattice Spacing (Å ± 0.04) |
|---|---|---|
| 7.0 | Medium | 12.70 |
| 9.0 | Strong | 9.87 |
| 12.6 | Very Strong | 7.00 |
| 20.2 | Strong | 4.39 |

Another aspect of the present invention is the provision of a crystalline Tosylate salt form (Tosylate Form I) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table IV, expressed in terms of diffraction angle (in 2θ), lattice "d" spacing (in angstroms) and relative peak intensities ("RI"):

TABLE IV

| Diffraction angle (2θ, ±0.2) | RI | Lattice Spacing (Å ± 0.04) |
|---|---|---|
| 9.4 | Medium | 9.36 |
| 20.0 | Very Strong | 4.43 |
| 21.0 | Medium Strong | 4.22 |
| 25.3 | Medium Strong | 3.51 |

Another aspect of the present invention is the provision of a crystalline Tosylate salt form (Tosylate Form I) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table V expressed in terms of diffraction angle (in 2θ), lattice "d" spacing (in angstroms) and relative peak intensities ("RI"):

TABLE V

| Diffraction angle (2θ, ±0.2) | RI | Lattice Spacing (Å ± 0.04) |
|---|---|---|
| 5.0 | Very Strong | 17.66 |
| 10.0 | Strong | 8.80 |
| 13.6 | Medium | 6.52 |
| 19.7 | Very Strong | 4.49 |

Another aspect of the present invention is the provision of a crystalline Tosylate salt form (Tosylate Form III) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table VI, expressed in terms of diffraction angle (in 2θ), lattice "d" spacing (in angstroms) and relative peak intensities ("RI"):

TABLE VI

| Diffraction angle (2θ, ±0.2) | RI | Lattice Spacing (Å ± 0.04) |
|---|---|---|
| 6.3 | Medium | 14.02 |
| 9.7 | Very Strong | 9.13 |
| 20.2 | Strong | 4.39 |
| 22.2 | Strong | 4.00 |

Another aspect of the present invention is the provision of a crystalline Tosylate salt form (Tosylate Form IV) of (5S,8S)-8-[{(1R)-1-(3,5-Bis-(trifluoromethyl)phenyl)-ethoxy}-methyl]-8-phenyl-1,7-diazaspiro[4.5]decan-2-one which is characterized by the x-ray powder diffraction pattern shown in Table VII, expressed in terms of diffraction angle (in 2θ), lattice "d" spacing (in angstroms) and relative peak intensities ("RI"):

TABLE VII

| Diffraction angle (2θ, ±0.2) | RI | Lattice Spacing (Å ± 0.04) |
|---|---|---|
| 6.1 | Strong | 14.44 |
| 9.6 | Strong | 9.19 |
| 20.9 | Strong | 4.26 |
| 22.0 | Strong | 4.03 |

Another aspect of the invention is the provision of pharmaceutical compositions containing at least one crystalline salt form of ((5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) selected from hydrochloride monohydrate form I salt, anhydrous hydrochloride forms I and II salts, and tosylate forms I, II and III salts, and the provision of methods of treating and/or preventing nausea and emesis by administering a medicament containing one or more of a crystalline salt forms of the compound of Formula I. In some embodiments it is preferred to coadminister a salt of the compound of Formula I prepared in accordance with the present invention with other therapeutic agents, for example, a chemotherapeutic agent, for example, temozolomide and cisplatin, preferably temozolomide.

In some embodiments it is preferred to administer additional therapeutic agents in a dosing regime selected from contemporaneous and simultaneous administration of additional therapeutic agents contained in a separate dosage form. In some embodiments it is preferred to administer additional therapeutic agents along with a salt of the present invention by simultaneous administration using a dosage form containing at least one salt of the present invention along with one or more therapeutic agents.

In some embodiments it is preferred to provide therapy by administering a medicament comprising the crystalline hydrochloride monohydrate salt form I of (5S,8S)-8-[[(1R)-1-(3,5-Bis-trifluoromethyl)phenyl]-ethoxymethyl]-8-phenyl-1,7-diazaspiro[4.5]decan-2-one in an amount providing a therapeutically effective serum level of the compound of Formula I or its salt in the treatment and/or prevention of nausea and emesis.

DETAILED DESCRIPTION OF THE INVENTION

Figure 1:
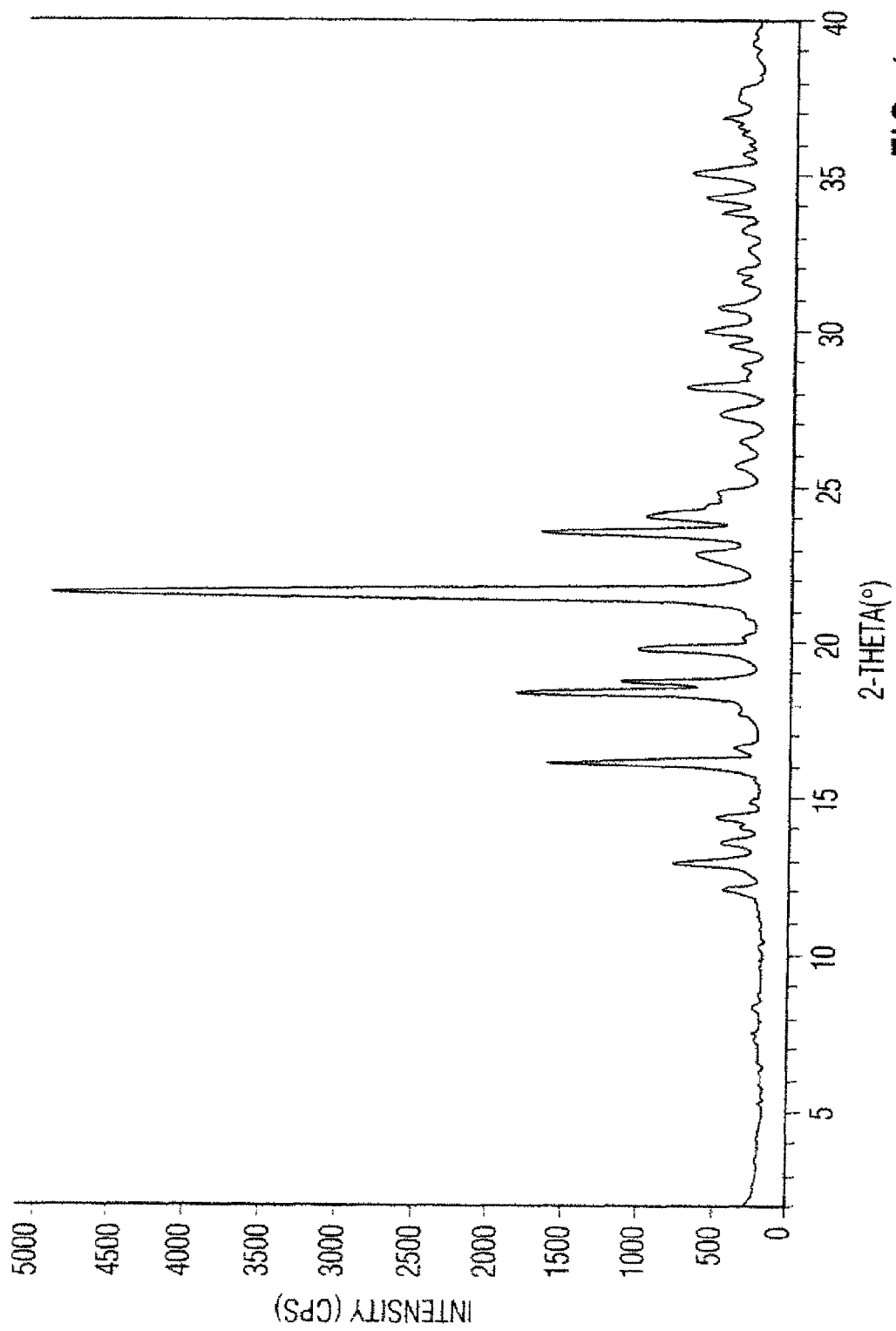
FIG. 1 presents a characteristic x-ray powder diffraction pattern of the crystalline hydrochloride monohydrate salt form of the compound of Formula I [Vertical Axis: Intensity CPS, counts (square root)); Horizontal Axis: Two Theta (2θ) (degrees)].

Salt forms of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) provide a therapeutic agent beneficial in the treatment of nausea and emesis.

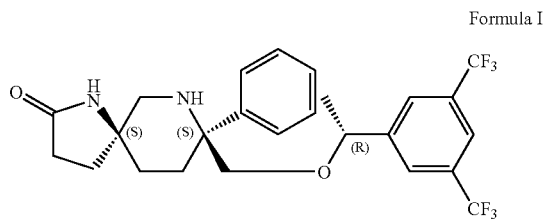

Formula I

The preparation of salts of (5S,8S)-8-[[(1R)-1-(3,5-Bis-trifluoromethyl)phenyl]-ethoxymethyl]-8-phenyl-1,7-diazaspiro[4.5]decan-2-one (the compound of Formula I), including the monohydrate hydrochloride salt of Formula II (shown above) and various tosylate salts, having physical and chemical properties useful in the provision of medicaments are disclosed in U.S. application Nos. 60/789,280 and 60/789,513, each of which is incorporated herein in its entirety by reference.

Two of the most debilitating side effects of cytotoxic chemotherapy are nausea and vomiting (emesis). There is both acute-phase chemotherapy induced nausea and emesis (CINE) and delayed-phase CINE. Acute-phase CINE occurs in the first 24 hours after chemotherapy administration while delayed-phase CINE manifests from between 2 days and 5 days post chemotherapy administration. Acute-phase CINE has been managed by administering 5HT3 receptor antagonists, often in combination with a corticosteroid, for example, dexamethasone, this treatment has not been effective in managing delayed-phase CINE. It is believed that acute-phase CINE and delayed-phase CINE arise from different physiological phenomena. It is believed that administration of an NK-1 receptor antagonist, for example, salts of (5S,8S)-8-[[(1R)-1-(3,5-Bis-trifluoromethyl)phenyl]-ethoxymethyl]-8-phenyl-1,7-diazaspiro[4.5]decan-2-one, either alone or in combination with one or more of a corticosteroid, for example, dexamethasone and/or a 5HT3 receptor antagonist, for example, ondensetron, granisetron, palonosetron, dolasetron, or tropisetron will provide a therapy effective in treatment of CINE in humans.

The salts of (5S,8S)-8-[[(1R)-1-(3,5-Bis-trifluoromethyl)phenyl]-ethoxymethyl]-8-phenyl-1,7-diazaspiro[4.5]decan-2-one are useful in the provision of therapy to address CINE and other conditions amenable to treatment by the administration of an NK-1 inhibitor, for example, nausea and/or emesis due to other causative factors, for example, motion sickness and morning sickness. Optionally, a formulation containing one of the salts of the present invention, when administered in an effective dosage amount, and optionally, administered along with a separate medicament containing either a 5HT3 receptor antagonists, for example, ondensetron, granisetron, palonosetron, dolasetron, or tropisetron and/or one or more corticosteroid, for example, dexamethasone, will be useful in the management of CINE. Optionally, a formulation containing a salt of the invention can additionally include one or more 5HT3 receptor antagonist, for example ondensetron, granisetron, palonosetron, dolasetron, or tropisetron, and/or one or more corticosteroid, for example, dexamethasone, in the provision of therapy in the treatment of both acute-phase and delayed-phase CINE.

The invention further provides a method of treating nausea and/or emesis. It is believed that medicaments comprising salts of the compound of Formula I are useful in the provision of anti-nausea and anti-emesis treatment for nausea and emesis arising from any cause, for example, arising from chemotherapy, from radiation therapy, arising during a post-operative recovery period, arising from motion sickness, arising from morning sickness, and arising from inner ear disturbances and infections. However, it is believed that the compound of Formula I is most advantageously employed in the provision of anti-nausea and/or anti-emesis treatment for delayed onset nausea and/or emesis associated with chemotherapy treatments, radiation treatments, and arising during a post-operative period. In some embodiments it is preferred to provide a combination of a salt of the compound of Formula I prepared in accordance with the present invention, or a pharmaceutical composition containing the salt, and other therapeutic agents, for example, a chemotherapeutic agent, for example, temozolomide and cisplatin, preferably temozolomide.

As used herein a combination includes: physically combined therapeutic agents in a pharmaceutical composition for administering in a single dosage form; a medicament or kit containing multiple therapeutic agents in one or more containers; and providing therapy that includes providing a therapeutically effective level of the compound of Formula I and other therapeutic agents, for example, by contemporaneous or simultaneous administration, as described herein, of more than one therapeutic agent. When a kit combination is provided, generally multiple medicaments are supplied in a form that will provide, upon administration to a patient in need of such therapy, a therapeutically effective amount of the active pharmaceutical ingredient(s) contained therein.

Coadministration can be carried out by contemporaneous administration of additional therapeutic agents, that is, administering a second medicament before, during, or after administration of a medicament comprising one or more of the salt forms of the present invention, where the second medicament contains one or more additional therapeutic agents in one or more additional dosage forms. Coadministration of additional therapeutic agents can also be carried out by simultaneous administration of multiple therapeutic agents contained in a single dosage form. An example of the latter administration scheme is a capsule dosage form containing one or more salts of the present invention together with one or more additional therapeutic agents, for example, a 5 HT-3 inhibitor, or a chemotherapeutic agent, for example, temozolomide. In some dosage forms containing more than one therapeutic agent it is preferred to prepare the formulation contained in the dosage form by introducing an admixture of all therapeutic agents into the formulation in place of the single drug substance, for example, an admixture of all of the drug substances to be included in the dosage form in place of a salt of the present invention.

Whether administered as a separate medicament, or included in the formulation of the present invention, when utilized it is preferred for the 5HT3 receptor antagonist to be selected from ondensetron, granisetron, palonosetron, dolasetron, and tropisetron, and when utilized, whether as a separate medicament or included in the formulation of the present invention, it is preferred for the corticosteroid to be selected from dexamethasone.

The present formulation can also contain additional therapeutic agents, for example, chemotherapeutic agents, for example, temozolomide, providing a single medicament for administering chemotherapeutic treatment and relief and/or prevention of nausea and/or vomiting associated with such chemotherapeutic agent administration. Examples of dosage levels of temozolomide are described in U.S. Pat. No. 5,939,098 (the '098 patent), issued Aug. 17, 1999, European Patent 0858341B1 (the '341 patent), Grant date Oct. 24, 2001, and published U.S. patent application no. 2006/0100188, published May 11, 2006 (the '188 publication). Each of the '098 patent and '341 patent describes coadministration of temozolomide with a 5HT3 inhibitor to provide therapy for immediate onset nausea and vomiting associated with chemotherapy. The '188 publication, in Tables 1 and 2 (pages 2 to 3 therein) describes detailed dosing regimens for dosing temozolomide.

It is believed also that this medicament may be useful in the treatment of other conditions amenable to treatment by administration of an NK-1 inhibitor, including, but not limited to, cough, morning sickness, and nausea and/or vomiting arising from motion sickness.

In addition to the compounds of the present invention being useful in the provision of anti-nausea and anti-emesis treatment, the salt forms disclosed herein have processing advantages related to their improved solubility in polar solvents in comparison to the free base form of the compound which are beneficial in the provision of useful medicaments. Moreover, each of the toyslate and hydrochloride salts have one or more crystalline forms which provide the compound of Formula I in a form having the following advantages compared to amorphous forms of the compound: lower impurity content and more consistent product quality i.e., more consistent physical characteristics including more consistent color, rate of dissolution and ease of handling; as well as a longer term stability when incorporated into a medicament.

As described in detail below, each of the crystalline salt forms of the compound of Formula I described herein can readily be distinguished from one another and from amorphous forms by examination of one or more of the characteristic X-ray Diffraction patterns (see FIGS. 1, 5, 6, 9, and 12 to 14), the characteristic infrared spectra (see FIGS. 3, 8, 11, 16, and 18) and the analytical Differential Scanning Calorimetry (DSC) thermograms (FIGS. 4, 19, 20, and 21) of the respective salt forms.

The inventors have surprisingly discovered that diazaspirodecan-2-ones of Formula I contain can be precipitated by inorganic acids selected from p-toluene-sulfonic acid

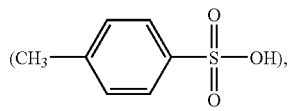

to form the tosylate salts of the compound of Formula I, and hydrochloric acid (HCl), to form hydrochloride salts of the compound of Formula I, for example, the hydrochloride monohydrate of Formula II. Unexpectedly, these salts can be precipitated in a crystalline solid form which optionally includes one or more solvent molecules in the crystal structure for each molecule of the protonated compound of Formula I present in the crystal structure. Examples of suitable solvent molecules which the inventors have found can form a part of the crystal structure are water, hexane and acetonitrile.

The salts of the present invention offer a number of surprising advantages over the free base in their physical properties, for example, the ability to mill, micronize and solubilize the compound. It has been found that the salts of the present invention are thermodynamically robust in addition to having desirable solubility and handling characteristics, thus providing the compound of Formula I in a salt form which is easily incorporated into a medicament and which is stable under a wide variety of environmental conditions.

As is known, therapeutic agents typically display poor absorption rates when they have an aqueous solubility of less than about 10 mg/ml over a pH range of from about pH 1 to about pH 7. Moreover, when orally administered therapeutic agents display a solubility of less than about 1 mg/ml within this pH range, typically such agents exhibit dissolution-rate limited absorption since solubility and absorption are related in orally administered medicaments. Accordingly, the improved solubility properties of these salts are important for the provision of an orally administered form of a medicament designed to deliver the compound of Formula I as a therapeutic agent. Some salts of the invention display advantageous physical properties in addition to these desirable improved solubility properties, as described in detail below.

In general, a salt of the invention may be prepared from a compound of Formula I and an acid selected from toluene-sulfonic acid and hydrochloric acid in accordance with the following procedure:

i) with stirring, a 0.1 g quantity of the compound of Formula I (approximately 0.2 mMol) and an equivalent amount (i.e. 0.2 mMol) of the selected acid is dissolved in about 3 ml of anhydrous ethanol contained in a vessel;

ii) with continued stirring, anhydrous diethylether is added dropwise to the mixture until it becomes cloudy;

iii) an amount of anhydrous ethanol just sufficient to clear the cloudiness is added to the cloudy mixture (typically several drops);

iv) the stirring is discontinued and the vessel is covered with aluminum foil containing vent holes and left to stand quiescent for 24 to 48 hours during which time solids will precipitate;

v) at the end of the quiescent period the solids are recovered by filtration, washed with solvent, and then dried first in the air for a period of from about 1 to about 18 hours and then vacuum dried at ambient temperature under house vacuum overnight, yielding the salt of the compound of Formula I.

For some salts, solvate forms of various crystals are prepared in accordance with the following general procedure. A sample of the salt prepared by reactive crystallization in accordance with the above procedure, or recrystallization of a salt initially precipitated as an amorphous material utilizing the above-described general procedure and subsequently crystallized by seeding a slurry of the amorphous salt, is weighed into a vial, typically from about 10 mg to about 50 mg. A solvent selected from ethanol, isopropanol, acetonitrile, water, toluene, ethyl acetate, methylene chloride and hexane, in an amount sufficient to completely immerse the solids is added to the vial. The solids and solvent are stirred under ambient conditions a period of time sufficient to provide solvate crystals, for example, for about seven days. When solvate crystals have been prepared, a sample of the suspended solvate crystals is dropped onto a sample holder for use in a powder X-ray diffraction spectrometer and air dried. These samples are then analyzed by X-ray spectroscopy according to procedures described herein. Additional procedures for preparing inventive salts of the compounds of Formula I are described and exemplified below.

Analytical Procedures

Each of the crystalline salt forms of the compound of Formula I is characterized by one or more techniques including X-ray powder diffraction spectroscopy (PXRD), Infrared Spectroscopy (IR), and Raman Spectroscopy (Raman). Selected salt forms of compound I were also analyzed by differential scanning calorimetry (DSC), and/or further characterized by physical methods including solubility studies and stability studies.

X-Ray Powder Diffraction Spectroscopy

X-ray powder diffraction spectroscopy was obtained on samples using one of the following procedures. For the solvates prepared in accordance with the above-described procedure, analysis was carried out on a Rigaku spectrometer according to the following procedure.

For analysis of samples obtained using a Rigaku Miniflex spectrometer, the following procedure was employed (PXRD method I). Specimens analyzed by PXRD method I were lightly packed onto a low-background plate. The specimens were exposed to the room environment with ambient temperature and humidity. The Rigaku spectrometer was equipped with a six-plate carousel that rotated the specimen at 54 rpm, minimizing preferred orientations of the crystals in the sample studied. The Rigaku spectrometer was equipped also with a copper Kα radiation source utilized without a Kα2 filter. The spectrometer was equipped also with a variable divergence slit and 0.3 mm receiving slit. Scan range was carried out from 2.0 to 40 °2θ. Instrument calibration was verified using the Cu Kα1 peak for the 111 plane. During scanning, the step size was 0.02 degrees over step durations of 0.6 seconds. Data analysis was accomplished using Jade Plus (release 5.0.26) analysis software. The data ware smoothed with a Savitzky-Golay parabolic filter at 11 points. Typically "d" spacing values are accurate to within ±0.04 A.

X-ray Powder Diffraction spectroscopy analysis was obtained for some samples using a Bruker D8 diffractometer manufactured in 2002 (PXRD method II). The Bruker diffractometer was equipped with a parallel optic configuration utilizing a GÖBEL beam focusing mirror and a PSD detector equipped with a fixed radial soller slit. The Bruker diffractometer was used with an Anton Paar TTK450 temperature stage. The radiation source is copper (Kα). The divergence slits are fixed at 0.6 mm. The Bruker diffractometer utilized a top-loading brass block sample holder. PSD fast scan was used to scan from 4.00 to 39.9°. To obtain a diffraction pattern, specimens were loaded onto the sample holder and leveled with a glass microscope slide. The sample chamber temperature was set at 25° C., 30° C. or 120° C., under ambient humidity and not purged with nitrogen and not under vacuum. Instrument calibration was verified using mica standards. During scanning, the step size was 0.013 degrees to 0.02 degrees over step durations of 0.5 to 10 seconds. Data analysis was accomplished using EVA analysis software, version 7.0.0.1, supplied by Bruker® written by SOCABIM®. The data were smoothed by the software at 0.1 to 0.15.

Except for those solvate samples prepared in accordance with the above-described procedure, samples for analysis by X-ray Powder Diffraction ("PXRD"), were subjected to minimal preparation to prevent any form changes. Sample particles were lightly packed into the sample holder to insure that they formed a smooth surface and did not clump together. No solvents, drying or other preparation steps were used for other than the solvate samples prepared in accordance with the procedure described above.

Infrared Spectroscopy

Samples were characterized utilizing attenuated total reflectance (ATR) infrared spectroscopy using a Nicolet Instruments NEXUS 670 FTIR equipped with an Avatar Smart Miracle Attenuated Total Reflectance (ATR) sample compartment. Spectra were collected utilizing the following parameters: DTGS KBr Detector; KBr beam splitter; scanning range 600 cm−1 to 4000 cm−1; aperture setting 100; resolution 2; 100 scans/sample. The analysis was carried out by collecting a background spectrum, then placing reference standard or particulate sample (typically 3 mg to 5 mg of sample) on the ATR crystal and applying force to the sample with the instrument's pressure arm in accordance with the manufacturers recommendations. A spectrum of the specimen (reference or sample) was then obtained as a ratio of the background and specimen spectra utilizing the manufacturers proprietary software.

Raman Spectroscopy

Raman spectroscopic analysis (Raman) of the hydrochloride and tosylate salts of the invention was performed on a Thermo Electron Nicolet Almega Dispersive Raman spectrometer in high-resolution mode. Samples were contained in NMR sample tubes and spectra were obtained under the following conditions: Scanning range 4000 cm−1 to 90 cm−1; Exposure time 1.0 second; 100 sample and 100 background exposures; Excitation Laser at 785 nm/100% power level/ parallel laser polarization; Grating 1200 lines/mm; 100 micron slit; Camera temperature −50° C.

Differential Scanning Calorimetry

Calorimetric studies were conducted utilizing a modulated Differential Scanning Calorimeter (DSC) from TA instruments. DSC scans were run at a heating rate of 10 C/min. in an open aluminum pan under nitrogen flowing at a rate of 40 ml/min.

Solubility tests were conducted by placing an excess of the compound in an aliquot of the solvent of interest and allowing the slurry to equilibrate under the selected temperature conditions (typically ambient). When the solvent was water, pH was adjusted to the desired value with hydrochloric acid and sodium hydroxide. When the slurry mixture had equilibrated, the excess solids were centrifuged (water) or filtered (all other solvents) from the supernatant and the amount of compound which had been dissolved was quantified utilizing HPLC analysis of diluted aliquots of the supernatant liquid. Pharmaceutical grade solvents were employed.

Chemical stability tests were carried out on aliquots of the salt form of interest by placing a accurately weighed sample of the salt form of the compound of Formula I into a polyethylene bag. The bagged samples were enclosed in fiberboard tubes fitted with metal caps which were stored under the indicated conditions of humidity and temperature for the indicated time. Analysis was carried out by dissolving the contents of a vial and quantifying the amount of solute utilizing HPLC analysis. Where noted the aliquots were stored in capped amber vials under the conditions noted instead of polyethylene bags.

EXAMPLES

Hydrochloride and tosylate salt forms of the compound of Formula I were prepared as described below. As discussed below, each of the salt forms of the compound of Formula I were also characterized by various spectroscopic techniques including X-ray Powder Diffraction Spectroscopy, Infrared Spectroscopy, and Raman Spectroscopy, using the techniques described in detail above. Selected salt forms were analyzed for stability, solubility and other improved physical properties, including, for some salts, analysis by differential scanning calorimetry (DSC). Unless noted to the contrary, all reactive crystallizations, recrystallization, and slurry procedures described herein were carried out in commercially available solvents of the specified grade (generally pharmaceutical or food grade unless otherwise specified) and used as received (unless otherwise specified).

Preparation of the compound of Formula I (free base) suitable for use in the preparation of salts of the compound of Formula I described in the following examples was obtained either from the methods disclosed in the '320 patent or by the procedure described herein employing the compound of Formula III.

One suitable procedure for preparing the compound of Formula I, (5S,8S)-8-[{(1R)-1-(3,5-Bis-(trifluoromethyl)phenyl)-ethoxy}-methyl]-8-phenyl-1,7-diazaspiro[4.5]decan-2-one, for use in the preparation of the salts described herein, is described in the above-mentioned U.S. Pat. No. 7,049,320 (the '320 patent), utilizing as a precursor to the compound of Formula I, the compound 61 (see the '320 patent at col. 98, line 1 to col. 100, line 10), which is incorporated herein by reference in its entirety. The compound of Formula I for use in the preparation of salts in accordance with the present invention may also suitably be prepared in accordance with the procedures described in the application filed on Mar. 22, 2007, comprising precipitating the mesylate salt of the compound of Formula III by treating a toluene solution of the compound of Formula III with methyl sulfonic acid. Simultaneous cyclization and nitrate reduction of the compound of Formula III is carried out by treating the compound of Formula III with acetic acid in the presence of zinc metal to provide the free base of the compound of Formula I.

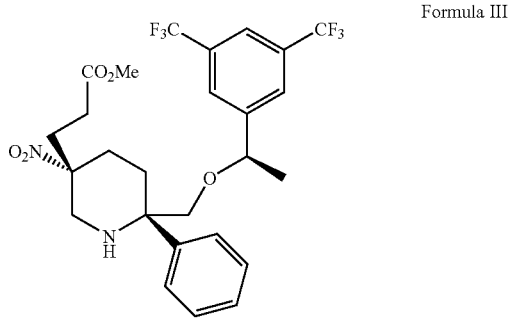 [SMILES: COC(=O)CC[C@@]1([N+](=O)[O-])CC[C@@](CO[C@H](C)c2cc(C(F)(F)F)cc(C(F)(F)F)c2)(c2ccccc2)NC1]

Formula III

The following example illustrates the foregoing process for converting the compound of Formula III into the compound of Formula I. Into a vessel was placed 8.14 Kg of the mesylate salt of the compound of Formula III (obtained by precipitation of the mesylate salt of the compound of Formula III, prepared in accordance with procedures described in the patent application filed on Mar. 20, 2007). With stirring, the salt of the compound of Formula III was dissolved in 82 L of concentrated acetic acid, and the temperature of the solution was adjusted to be from about 25° C. to about 30° C. In a separate reactor 12.2 Kg of zinc dust was placed under an inert nitrogen atmosphere by purging and venting the reactor 3 times. The zinc dust was then covered with 42 L of concentrated acetic acid during which the inert atmosphere was maintained. While maintaining the inert atmosphere, the zinc dust/acetic acid mixture was stirred to maintain substantially all of the zinc dust in suspension and slow addition of the acetic acid solution of the compound of Formula III was begun at a rate which maintained the temperature in the reaction vessel at no more than about 60° C. After all of the solution of the compound of Formula III had been added the reaction vessel temperature was maintained at a temperature of from about 55° C. to about 60° C. The reaction mixture temperature was maintained and vigorous stirring was continued to maintain suspension of the zinc until samples of the reaction mixture indicated that substantially all of the compound of Formula III was consumed.

When sampling indicated that the reaction had run to completion (less than about 5 mole % of uncyclized material present in the reaction mixture), the reaction mixture was cooled to a temperature of from about 30° C. to about 20° C. When the reaction mixture had cooled it was filtered through about 4.12 Kg of filteraid (Hyflo). The filter cake was washed with two 70 L aliquots of toluene which were combined with the filtrate previously obtained. The combined wash and filtrate was vacuum distilled at a pressure of from about 80 mbar to about 120 mbar and a temperature of from about 30° C. to about 60° C. The residue thus obtained was maintained under an inert atmosphere and redissolved in 41 L of toluene at ambient temperature.

The toluene solution of the residue was sequentially washed 45 L of 2N HCl aqueous solution followed by 80 L of 9 wt. % aqueous sodium carbonate (8 kg $Na_2CO_3$ in 82 L $H_2O$) followed by two successive 22 L aliquots of 10 wt % aqueous sodium chloride (2.2 Kg NaCl in 21 L $H_2O$). After completing the washing regime, the toluene supernatant solution was filtered through a 0.2 micron inline filter. The filter was rinsed with an additional 4 L of toluene which was combined with the supernatant liquid containing the free base compound of Formula I.

Provision of Hydrochloride Monohydrate Salt Form I Directly from the Formula III Compound Reaction Mixture The supernatant containing the free base compound of Formula I prepared from the compound of Formula III, as described above, was placed into a reactor and maintained at a temperature of from about 20° C. to about 25° C. Seed crystals of the hydrochloride monohydrate salt of the compound of Formula I were added to the supernatant in an amount of about 0.004 kg. After the solution had been seeded, 1.7 L of concentrated aqueous hydrochloric acid (37%) and 1.2 L of ethanol containing about 5 vol. % isopropanol (Fine Spirit® obtained from Thommen) were added over a period of about 20 minutes. The mixture was agitated for about 30 minutes. Agitation was continued and the mixture was cooled and maintained between a temperature of from 0° C. to about 5° C. The cold mixture was agitated for an additional 35 minutes. At the end of the agitation period the crystals thus obtained were isolated by vacuum filtration through a No. 148 filter and washed with 5 successive 5 L aliquots of a 1.1 (vol:vol) mixture of toluene and methyl tertiary butyl ether (MTBE) followed by a final wash comprising one 10 L aliquot of MTBE.

The precipitated monohydrate hydrochloride form I salt crystals were recovered from the filter and dried in a vacuum oven at a temperature of from about 40° C. to about 45° C. until the desired residual solvent (MTBE, ethanol, toluene and water) values were obtained.

Hydrochloride Salts of the Compound of Formula I

It was found that the amorphous hydrochloride salt for of the compound of Formula I, prepared by treating a solution of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) with hydrochloric acid, in accordance with the general procedure described above, could be converted to three crystalline forms of a salt of the compound of Formula I.

The Crystalline Monohydrate Hydrochloride Salt Form I of the Compound of Formula I Crystalline monohydrate hydrochloride form I salt was prepared directly from the compound of Formula I by dissolving one equivalent of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I prepared in accordance with the procedures described in the '320 patent) in a minimum of ethanol or methanol, and adding one equivalent of hydrochloric acid to the solution. Following the addition of HCl, water was added dropwise to the solution with stirring until crystals of the monohydrate hydrochloride salt form of the compound of Formula I dropped out of the solution. The crystals were separated from the supernatant liquid by filtration, washed with ethanol and vacuum dried.

Whether the HCl salt is obtained by precipitation of the free base of the compound of Formula I provided directly from reaction of the compound of Formula III described above, or provided by the procedures described in the '320 patent, or provided in another manner, a hydrochloride salt of the compound of Formula I can be recrystallized in accordance with the following procedure to provide the monohydrate hydrochloride crystal form I in accordance with the following procedure. Into a vessel was added, under a nitrogen blanket, 14.54 Kg of the monohydrate hydrochloride salt form I of the compound of Formula I prepared as described above. The crystals were suspended by adding a mixture consisting of: 35 L of Fine Spirits® (ethanol with 5 wt % isopropanol); 35 L water; 0.3 L concentrated HCl (37%) with agitation. The suspension was heated to reflux (approximately 78° C. to 85° C.) with continued agitation. When the solution was clear it was filtered through a No. 3 filter into a second vessel. The filter was rinsed with a water/ethanol mixture consisting of 10 L of Fine Spirits® and 32 L of water at a temperature of from about 60° C. to about 70° C. and the rinse was added to the filtrate solution. The temperature of the combined rinse and filtrate was stabilized at 73° C. (±1° C.) and 0.115 kg of monohydrate hydrochloride salt form I seed crystals were added with agitation. With continued agitation the temperature was maintained at about 73° C. for about 20 minutes additional. The solution was subsequently cooled at a rate of from about 0.5° C./min to a temperature between 0° C. and 5° C. and maintained at this temperature with agitation for 33 minutes while a thick suspension gradually formed. At the end of this time period the crystals were separated from the suspension by filtration through a No. 110 filter. The filter was washed with 14.5 L of an ethanol/water mixture (40:60, ethanol:water by vol) which had been chilled and maintained at a temperature between 0° C. and 5° C. The crystals were recovered from the filter and dried for about 15 hours in a vacuum drier with the temperature maintained between 35° C. and 40° C.

With reference to FIGS. 1 to 4, the monohydrate hydrochloride salt form I of the compound of Formula I prepared above was analyzed by X-ray, Infrared, and Raman spectroscopy and by DSC, as described above. Table VIII, below, lists 12 characteristic peaks of the X-ray Powder Diffraction spectrum shown in FIG. 1, expressed in diffraction angle expressed in degrees 2 theta (°2θ), the corresponding "d" spacing in angstroms (A), and relative intensities of the signal ("RI") in the following notation: S=strong, M=medium, W=weak, V=Very and D=diffuse:

TABLE VIII

| Diffraction Angle (°2 θ, ±0.2) | D spacing (A, ±0.04) | relative intensity |
| --- | --- | --- |
| 12.9 | 6.85 | VW |
| 16.1 | 5.49 | M |
| 18.4 | 4.83 | M |
| 18.7 | 4.74 | W |
| 19.8 | 4.48 | W |
| 21.6 | 4.11 | S |
| 22.8 | 3.89 | VWD |
| 23.5 | 3.78 | M |
| 24.0 | 3.70 | WD |
| 28.2 | 3.16 | VW |
| 34.3 | 2.62 | VW |
| 35.1 | 2.56 | VW |

Of the peaks characteristic of the monohydrate hydrochloride salt of the compound of Formula I shown in Table VIII, the eight most characteristic peaks are those appearing at diffraction angles (in °2θ) equal to 12.9, 16.1, 18.4, 18.7, 19.8, 21.6, 23.5, and 24.0, and the four most characteristic peaks are those appearing at diffraction angles (in °2θ) equal to 16.1, 18.4, 21.6, and 23.5.

Figure 2:
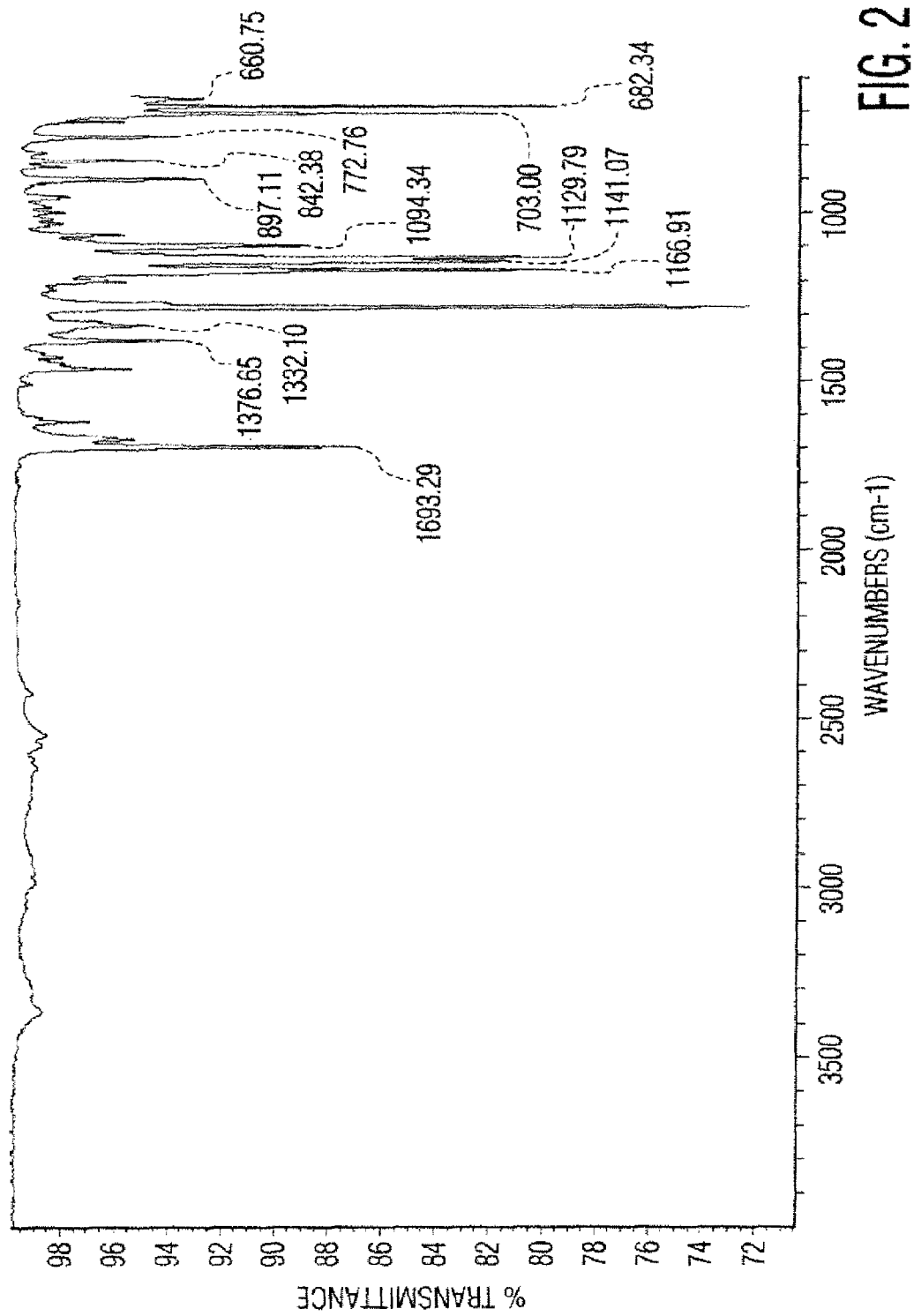
FIG. 2 presents a characteristic infrared spectrum of the crystalline hydrochloride monohydrate salt form of the compound of Formula I [Vertical Axis; Transmittance (Percent); Horizontal Axis: wavenumber (cm−1)].

FIG. 2 illustrates a transmission Infrared Spectrum of the crystalline monohydrate hydrochloride form I salt of the compound of Formula I, obtained in accordance with the above-described procedures. The 12 most characteristic peaks of the crystalline monohydrate hydrochloride form I salt shown in FIG. 2 are listed in Table IX, below, and in an adjacent column, the relative absorption intensity of each listed peak utilizing the notation: S=Strong, M=Moderate, W=Weak.

TABLE IX

| Absorption Peak | Wave No. (cm$^{-1}$) | relative intensity |
| --- | --- | --- |
| 1 | 1693 | M |
| 2 | 1377 | W |
| 3 | 1277 | S |
| 4 | 1167 | S |
| 5 | 1141 | S |
| 6 | 1130 | S |
| 7 | 1094 | M |
| 8 | 897 | W |
| 9 | 842 | W |
| 10 | 772 | W |
| 11 | 703 | S |
| 12 | 682 | S |

Of the characteristic peaks shown in Table IX, the 8 most characteristic peaks of the compound are those appearing at 1693, 1277, 1167, 1141, 1130, 1094, 703, and 682 reciprocal centimeters (cm$^{-1}$), and the four most characteristic peaks are those appearing at 1693, 1277, 1167, and 682 cm$^{-1}$.

Figure 3:
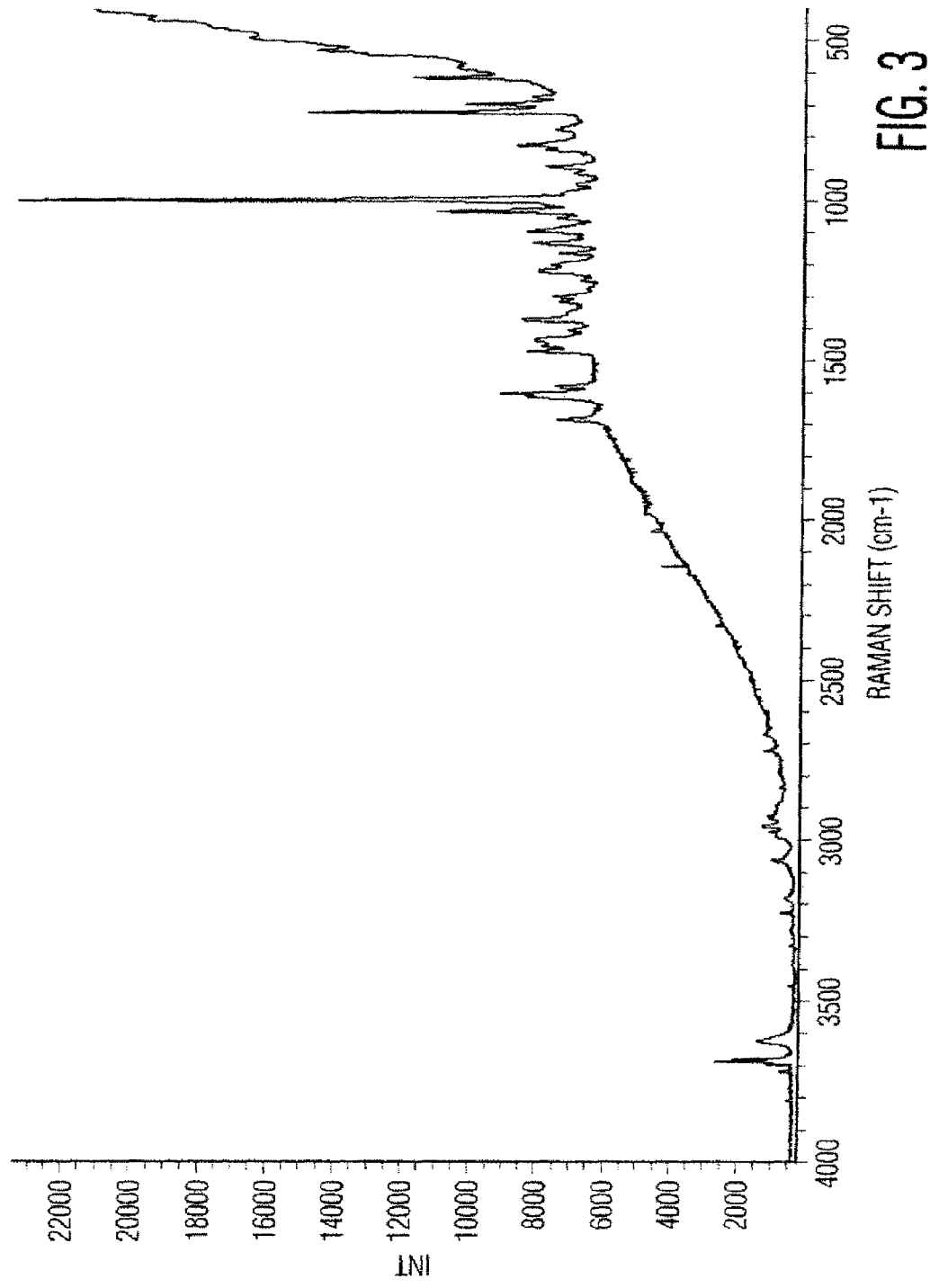
FIG. 3 presents a characteristic Raman spectrum of the crystalline hydrochloride monohydrate salt form of the compound of Formula I, [horizontal axis; Raman shift in reciprocal centimeters, vertical axis; relative intensity versus background]

FIG. 3 illustrates a Raman spectrum of the monohydrate hydrochloride form I salt of the compound of Formula I. The 12 most characteristic scattering peaks of the spectrum in FIG. 3 are listed (in reciprocal centimeters, cm$^{-1}$) in Table X (below). In a column adjacent to the listed peaks, the relative absorption intensity of each peak is indicated in the notation: S=Strong; M=Moderate; W=Weak; V=Very; B=Broad.

TABLE X

| Scattering Peak | Wave No. (cm$^{-1}$) | relative intensity |
| --- | --- | --- |
| 1 | 3695 | W |
| 2 | 3690 | W |

TABLE X-continued

| Scattering Peak | Wave No. (cm$^{-1}$) | relative intensity |
|---|---|---|
| 3 | 3625 | WB |
| 4 | 1604 | MB |
| 5 | 1371 | WB |
| 6 | 1218 | WB |
| 7 | 1032 | M |
| 8 | 997 | S |
| 9 | 827 | WB |
| 10 | 732 | VW |
| 11 | 698 | S |
| 12 | 616 | M |

Of the characteristic peaks shown in Table X, the 8 most characteristic peaks of the compound are those appearing at 3695, 3690, 3625, 1604, 1032, 997, 724, and 616 cm$^{-1}$, and the four most characteristic peaks are those appearing at 3695, 1032, 997, and 724 cm$^{-1}$.

Figure 22:
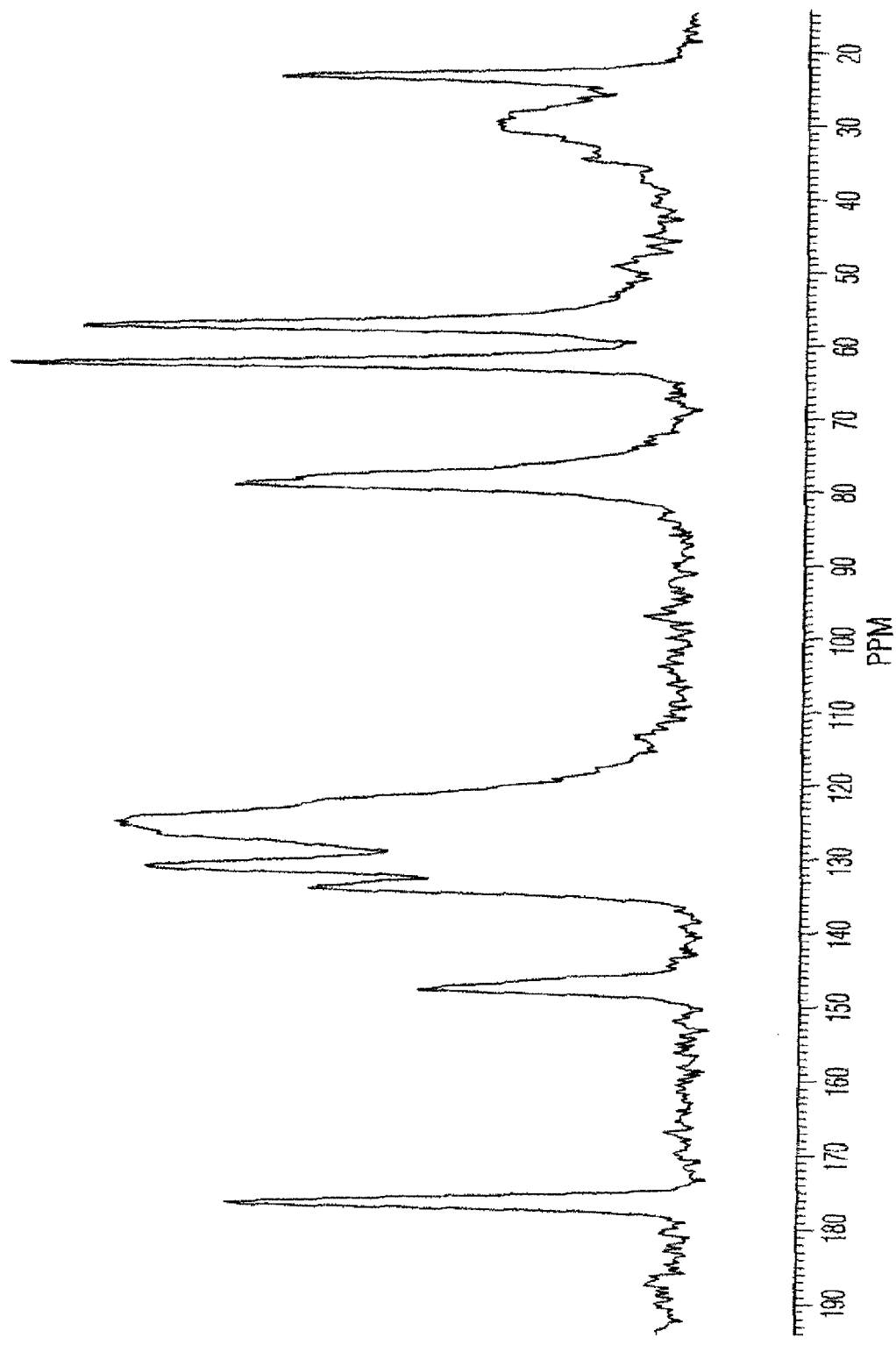
FIG. 22 presents a characteristic solution proton NMR spectrum of a hydrochloride salt of the compound of Formula I.

FIG. 22 presents a proton NMR spectra of the monohydrate hydrochloride form I salt of the compound of Formula I obtained by analyzing a solution of about 12 mg/ml of the salt dissolved in deuterated dimethyl sulfoxide. The spectrum was obtained by analyzing the solution with a Varian INOVA-500 NMR spectrometer at 25° C. Table XI lists the characteristic peaks of the spectrum in ppm relative to TMS. The region from 7.3 ppm to 8.0 ppm has the peaks expected for a mono-substituted aromatic ring and a symmetrical tri-substituted aromatic ring. The region from 8.5 ppm to 10.8 ppm is consistent with three amine peaks, including the protonated amine forming the HCl salt The region between 2.8 and 4.8 ppm is consistent with five aliphatic protons proximal to a nitrogen or oxygen. The region between 1.3 ppm and 2.6 ppm is consistent with the remaining eight aliphatic protons and the doublet at 1.4 ppm is consistent with the methyl group.

TABLE XI

Table 1 H-NMR Assignments

| Proton | Chemical Shift (PPM) | |
|---|---|---|
| 1-NH | 8.56 | Br |
| H3s | 2.15, 2.24 | m, m |
| H4s | 1.67, 1.88 | m, m |
| H6s | 2.88, 3.22 | d of d (10 Hz, 13 Hz) d (13 Hz), |
| 7NH$_2^+$ Cl$^-$ | 9.63, 10.62 | m, d (12 Hz), d of d (10 Hz, 12 Hz) |
| H92 | 2.19, 2.49 | m, d (14.5 Hz) |
| H10s | 1.39, 1.79 | m, d (13.5 Hz) |
| H12, 12' | 7.58 | d (7.5 Hz) |
| H13, 13' | 7.44 | M |
| H14 | 7.40 | M |
| H15s | 3.36, 4.30 | d (10 Hz), d (10 Hz) |
| H16 | 4.65 | q (6.4 Hz) |
| H17s | 1.41 | d (6.4 Hz) |
| H19, 19' | 7.66 | S |
| H21 | 7.92 | S |

Figure 4:
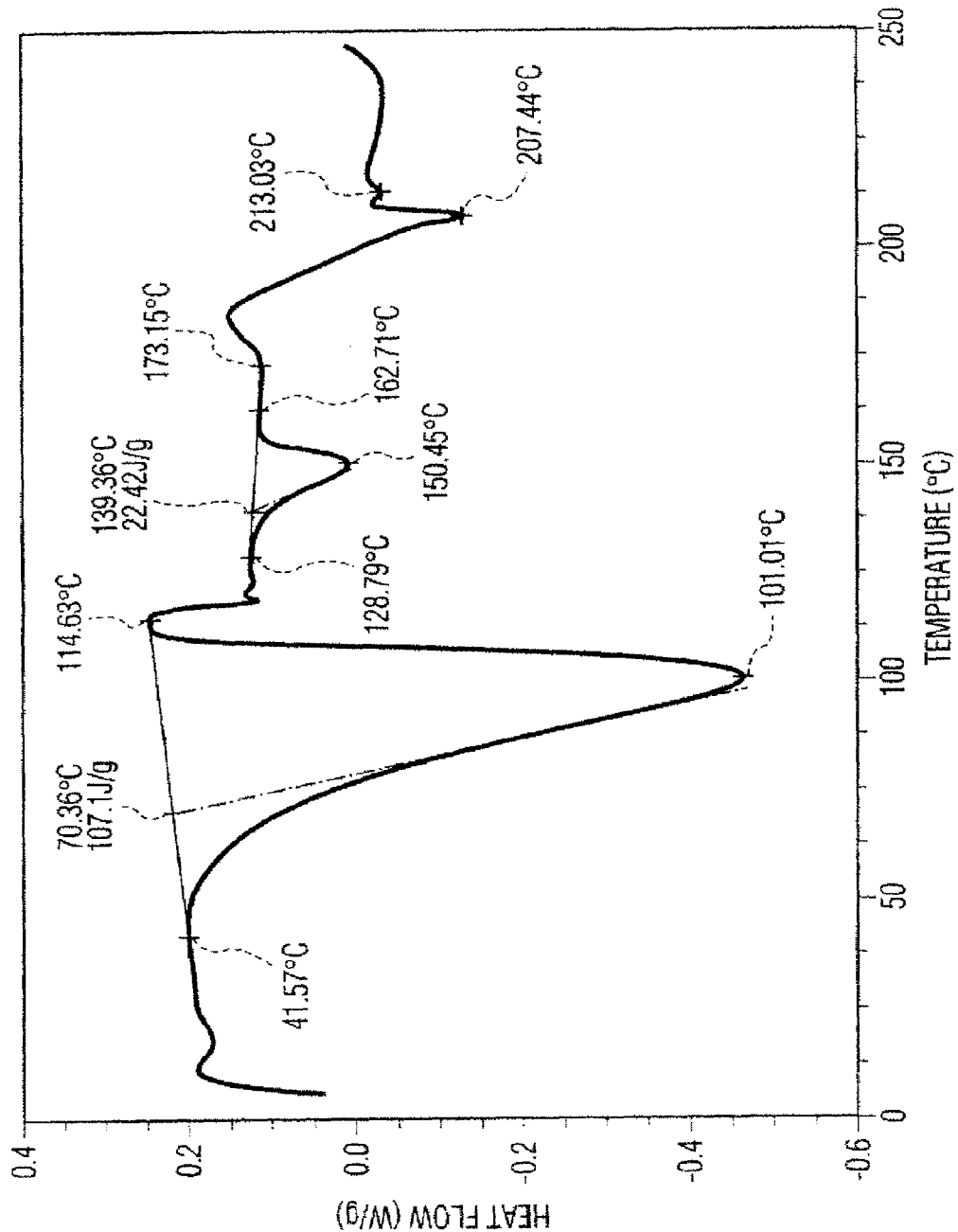
FIG. 4 presents a characteristic differential scanning calorimetry thermogram of the crystalline hydrochloride monohydrate salt form of the compound of Formula I, [Vertical Axis; Heat Flow in cal/sec/g; Horizontal Axis: Temperature in degrees centigrade].

The crystalline monohydrate hydrochloride form I salt of the compound of Formula I was analyzed by differential scanning calorimetric in accordance with the procedures described above. FIG. 4 illustrates the DSC thermogram obtained from this analysis. The DSC thermogram of FIG. 4 contains a broad endotherm centered at approximately 101° C., a second endotherm centered at approximately 150° C., and a third endotherm centered at approximately 207° C. The first endotherm corresponds to dehydration of the crystalline monohydrate form I, producing the corresponding anhydrous hydrochloride form I salt. The second endotherm corresponds to the melting of the anhydrous form I salt (about 150° C.), which in melting decomposes to produce anhydrous hydrochloride form II salt. The third endotherm at approximately 207° C. corresponds to the anhydrous form II salt melting point.

The inventors have found that when the monohydrate hydrochloride form I salt was dehydrated at a temperature below the decomposition point of the anhydrous hydrochloride form I salt, subsequent storage of anhydrous form I salt under ambient conditions of temperature and humidity returns the crystals to the monohydrate form. Stability test in accordance with the above-described procedure showed that the monohydrate hydrochloride form I salt of the compound of Formula I does not decompose or dehydrate under conditions of ambient temperature and at relative humidity of from about 5% relative humidity to about 95% relative humidity.

Figure 5:
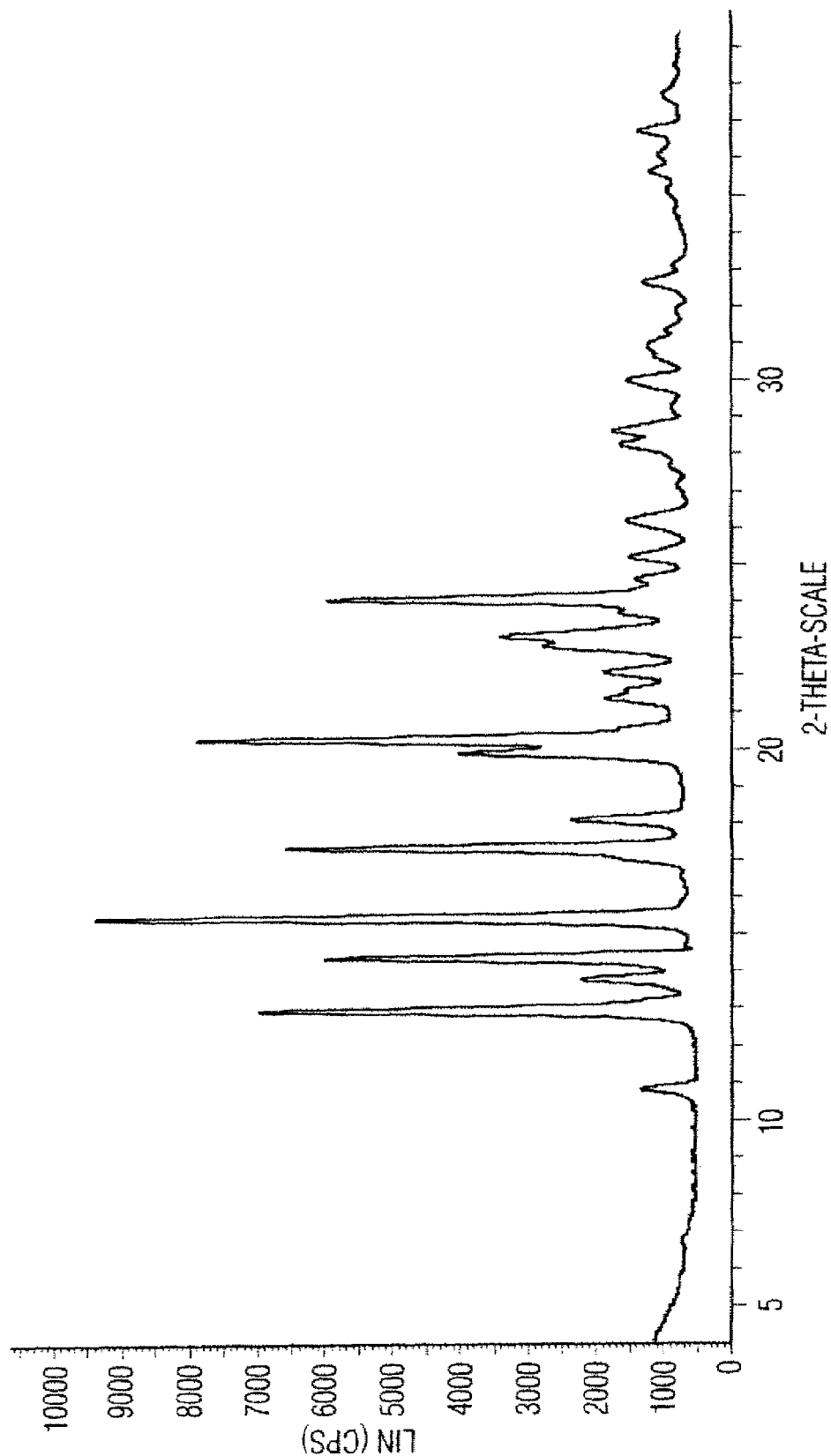
FIG. 5 presents a characteristic x-ray powder diffraction pattern of the crystalline hydrochloride anhydrous salt form I of the compound of Formula I, [Vertical Axis: Intensity (CPS, counts (square root)); Horizontal Axis: Two Theta ((2θ) degrees)].

A sample of the anhydrous form I salt was prepared by heating the monohydrate hydrochloride form I salt of the compound of Formula I under flowing nitrogen at a temperature above 70° C. The anhydrous form I salt was analyzed by X-ray Powder Diffraction Spectroscopy. FIG. 5 illustrates an X-ray Powder Diffraction Spectrum of the anhydrous hydrochloride form I salt of the compound of Formula I. Table XII, below, lists 12 characteristic peaks of the spectrum shown in FIG. 5 by diffraction angle expressed in degrees 2 theta (°2θ), the corresponding "d" spacing in angstroms (A), and relative intensities of the signal ("RI") in the following notation: S=strong, M=medium, W=weak; V=Very and D=diffuse:

TABLE XII

| Diffraction Angle (°2 θ, ±0.2) | d spacing (A, ±0.04) | relative intensity |
|---|---|---|
| 10.8 | 8.21 | VW |
| 12.9 | 6.86 | S |
| 13.7 | 6.45 | W |
| 14.3 | 6.18 | S |
| 15.4 | 5.75 | S |
| 17.3 | 5.13 | S |
| 18.0 | 4.91 | W |
| 19.9 | 4.47 | M |
| 20.2 | 4.39 | S |
| 22.0 | 4.03 | W |
| 23.0 | 3.86 | M |
| 24.0 | 3.70 | S |

Of the peaks characteristic of the anhydrous form I hydrochloride salt of the compound of Formula I shown in Table XII, the eight most characteristic peaks are those appearing at diffraction angles (in °2θ) equal to 12.9, 14.3, 15.4, 17.3, 19.9, 20.2, 23.0, and 24.0, and the four most characteristic peaks are those appearing at diffraction angles (in °2θ) equal to 12.9, 15.4, 17.3, and 20.2.

Figure 6:
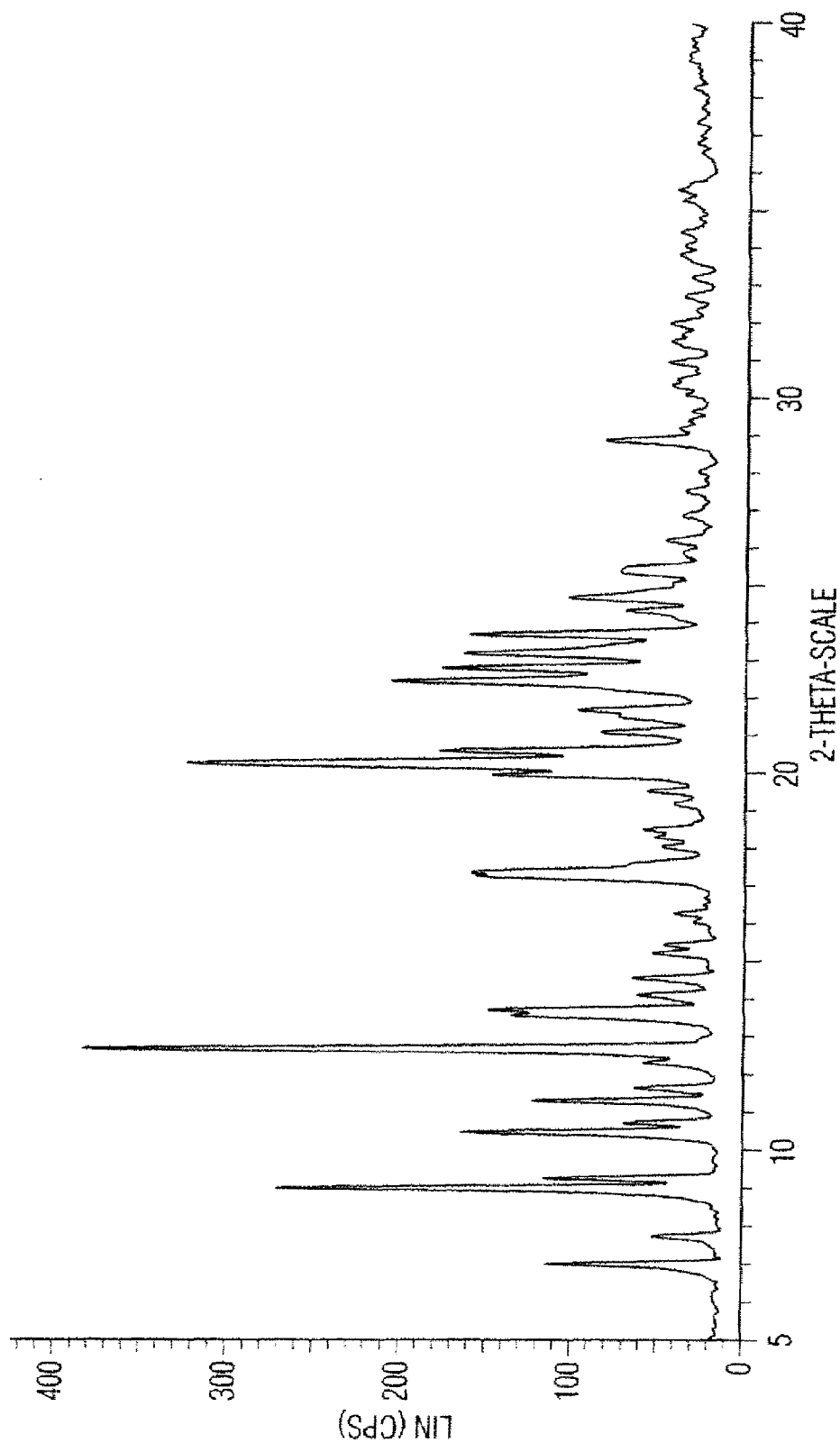
FIG. 6 presents a characteristic x-ray powder diffraction pattern of the crystalline hydrochloride anhydrous salt form II of the compound of Formula I, [Vertical Axis: Intensity (CPS, counts (square root)); Horizontal Axis: Two Theta ((2θ) degrees)].

FIG. 6 illustrates an X-ray Powder Diffraction spectrum of the anhydrous hydrochloride form II salt of the compound of Formula I prepared by heating the anhydrous form I hydrochloride salt above its decomposition point. Table XIII, below, lists 12 characteristic peaks of the X-ray Powder Diffraction spectrum shown in FIG. 6 by diffraction angle expressed in degrees 2 theta (°2θ), the corresponding "d" spacing in angstroms (A), and relative intensities of the signal ("RI") in the following notation: S=strong, M=medium, W=weak; B=Broad, V=Very and D=diffuse:

TABLE XIII

| Diffraction Angle (°2 θ, ±0.2) | d spacing (A, ±0.04) | relative intensity |
|---|---|---|
| 7.0 | 12.70 | M |
| 9.0 | 9.87 | S |
| 10.4 | 8.48 | M |
| 11.3 | 7.85 | M |
| 12.6 | 7.00 | S |
| 13.7 | 6.47 | MD |
| 17.3 | 5.13 | WD |
| 20.2 | 4.39 | S |
| 22.4 | 3.96 | M |
| 22.8 | 3.90 | M |
| 23.2 | 3.83 | M |
| 23.7 | 3.75 | M |

Of the peaks characteristic of the anhydrous form II hydrochloride salt of the compound of Formula I shown in Table XIII, the eight most characteristic peaks are those appearing at diffraction angles (in °2θ) equal to 7.0, 9.0, 10.4, 12.6, 13.7, 17.3, 20.2, and 22.4, and the four most characteristic peaks are those appearing at diffraction angles (in °2θ) equal to 7.0, 9.0, 12.6, and 20.2.

Figure 7:
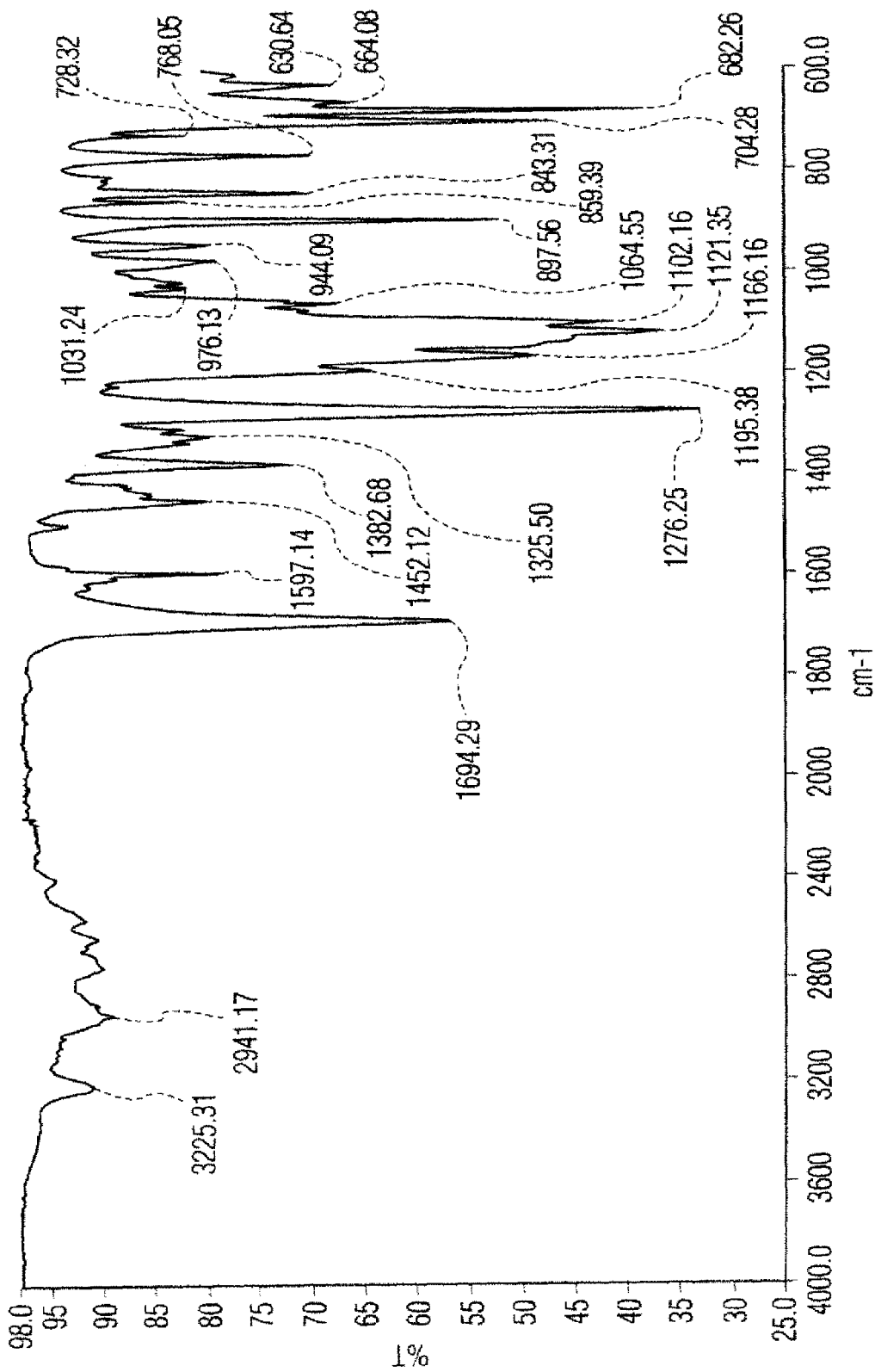
FIG. 7 presents a characteristic infrared spectrum of the crystalline hydrochloride anhydrous salt form II of the compound of Formula I [Vertical Axis; Transmittance (Percent); Horizontal Axis: wavenumber (cm−1)].

FIG. 7 illustrates a transmission infrared spectrum of the crystalline anhydrous hydrochloride form II salt form of the compound of Formula I obtained in accordance with the procedures described above. The 12 most characteristic peaks of the crystalline monohydrate are listed in Table XIV, below, and in an adjacent column, the relative absorption intensity of each listed peak utilizing the notation: S=Strong, M=Moderate, W=Weak.

TABLE XIV

| Absorption Peak | Wave No. (cm$^{-1}$) | relative intensity |
|---|---|---|
| 1 | 1694 | M |
| 2 | 1597 | W |
| 3 | 1383 | W |
| 4 | 1276 | S |
| 5 | 1066 | M |
| 6 | 1020 | S |
| 7 | 1102 | S |
| 8 | 898 | M |
| 9 | 843 | M |
| 10 | 768 | M |
| 11 | 704 | S |
| 12 | 682 | S |

Of the characteristic peaks shown in Table XIV, the 8 most characteristic peaks of the compound are those appearing at 1694, 1597, 1276, 1166, 1120, 898, 704 and 682 reciprocal centimeters (cm$^{-1}$), and the four most characteristic peaks are those appearing at 1694, 1276, 898, and 682 cm$^{-1}$.

Figure 8:
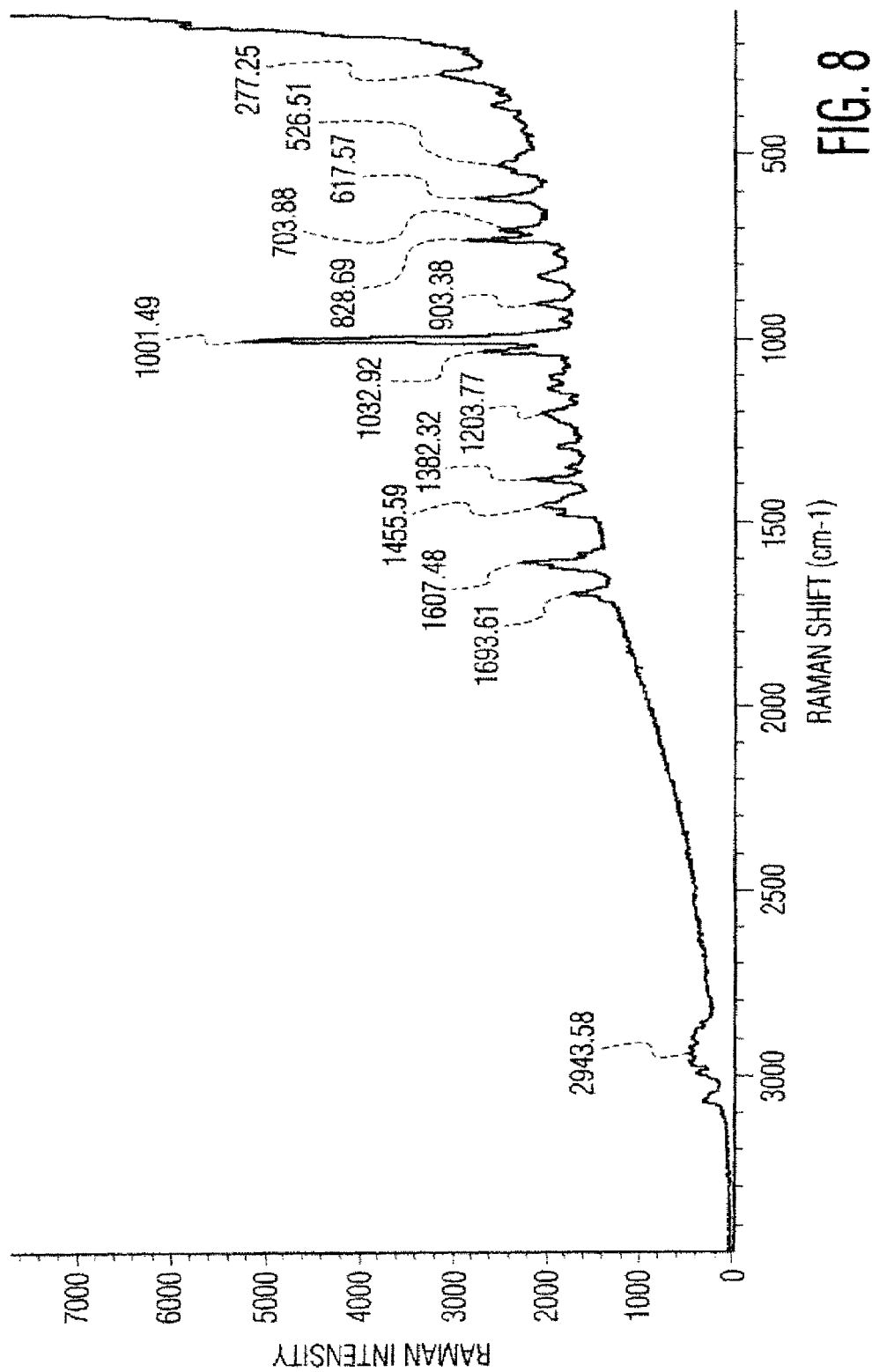
FIG. 8 presents a characteristic Raman spectrum of the crystalline hydrochloride anhydrous salt form II of the compound of Formula I, [horizontal axis; Raman shift in reciprocal centimeters, vertical axis; relative intensity versus background]
Figure 9:
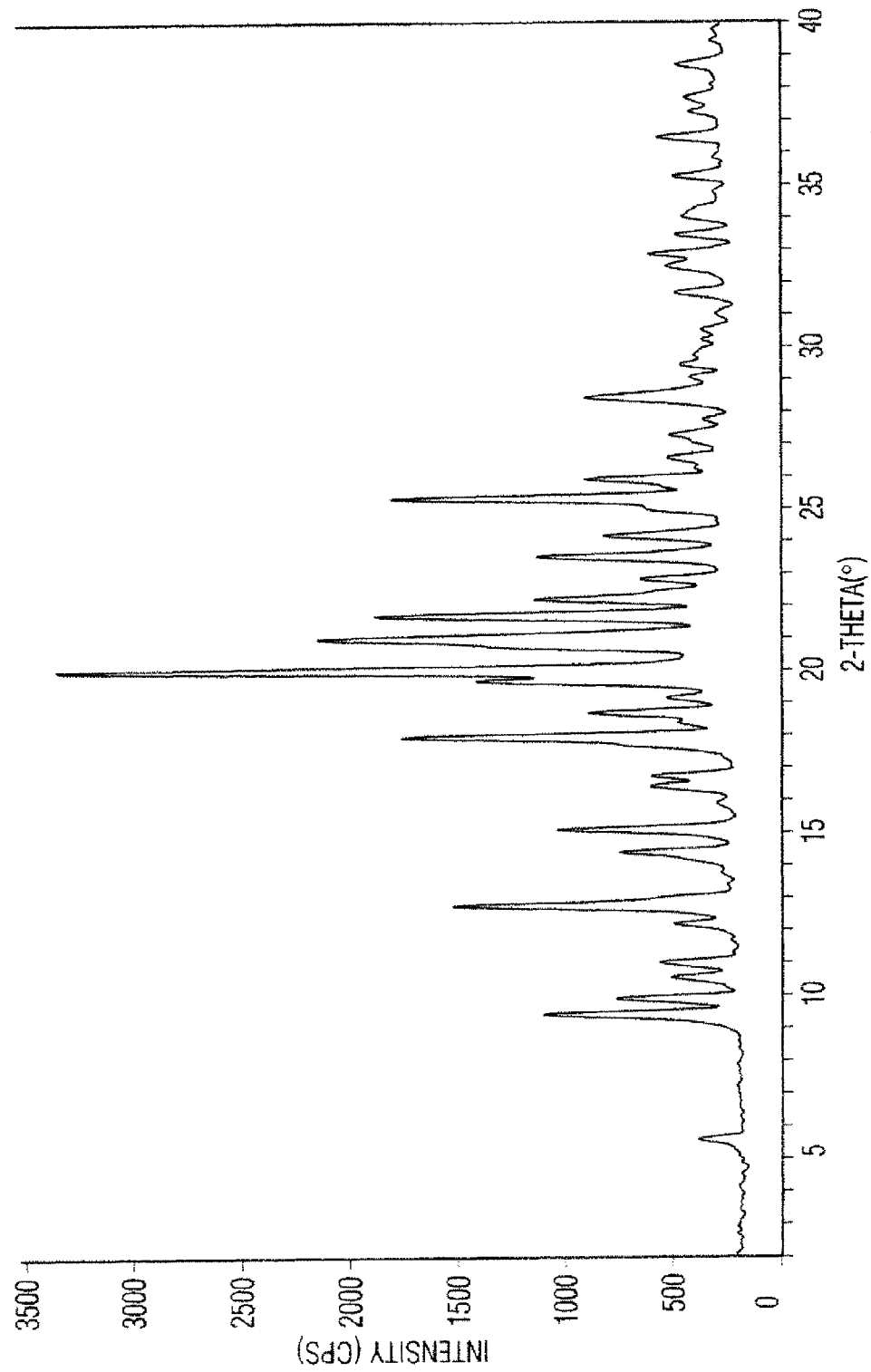
FIG. 9 presents a characteristic x-ray powder diffraction pattern of the crystalline tosylate salt form I of the compound of Formula I, [Vertical Axis: Intensity (CPS, counts (square root)); Horizontal Axis: Two Theta ((2θ) degrees)].

FIG. 8 illustrates a Raman spectrum of the anhydrous hydrochloride form II salt form of the compound of Formula I obtained in accordance with the above described procedures. Table XV, below, lists the 12 most characteristic scattering peaks (in reciprocal centimeters, cm$^{-1}$) of the compound shown in the spectrum of FIG. 8. In a column adjacent to the listed peaks, the relative absorption intensity of each peak is indicated in the notation: S=Strong; M=Moderate; W=Weak; V=Very; B=Broad.

TABLE XV

| Scattering Peak | Wave No. (cm$^{-1}$) | relative intensity |
|---|---|---|
| 1 | 1694 | W |
| 2 | 1607 | M |
| 3 | 1456 | W |
| 4 | 1382 | W |
| 5 | 1033 | M |
| 6 | 1001 | S |
| 7 | 903 | W |
| 8 | 829 | W |
| 9 | 729 | W |
| 10 | 618 | W |
| 11 | 527 | WB |
| 12 | 277 | W |

Of the characteristic peaks shown in Table XV, the 8 most characteristic peaks of the compound are those appearing at 1694, 1607, 1456, 1382, 1001, 729, 618, and 277 cm$^{-1}$, and the four most characteristic peaks are those appearing at 1607, 1001, 729, and 277 cm$^{-1}$.

When examined for solubility in accordance with the above-described procedure, it was found that the monohydrate hydrochloride form I salt of the compound of Formula I had aqueous solubility, at pH of 4 or less (more acidic), of at least about 1.0 mg/ml, and had the indicated solubilities at ambient temperatures in the pharmaceutical solvents shown below in Table XVI.

TABLE XVI

| Solvent | Solubility (mg/ml, ambient conditions) |
|---|---|
| Ethanol | 185 |
| Propylene Glycol | 160 |
| PEG 400 ™ | 20 |
| Glycerin | 16 |

The stability of the crystalline monohydrate hydrochloride salt form of the compound of Formula I was also examined using the procedure described above for samples contained in polyethylene bags by exposing samples to the following conditions: (a) 60% relative humidity (RH) at 4° C. for twelve months, at 25° C. for eighteen months, and at 50° C. for one month; (b) 40° C. and 75% relative humidity (RH) for twelve weeks, and (c) 70° C. at ambient humidity for one hour. Samples of the crystalline monohydrate hydrochloride form I salt were also tested for one cycle of ICH UV/Vis light stress conditions. These tests demonstrated that the crystalline monohydrate hydrochloride form I salt of the compound of Formula I is stable at room temperature between about 5% and about 95% relative humidity, is stable up to about 70° C., and is stable under light stress conditions.

Tosylate Salts of the Compound of Formula I

In accordance with the processes described herein, four forms of a tosylate salt of the compound of Formula I have been prepared.

Tosylate Form I Salt

Crystalline tosylate form I salt of the compound of Formula I was prepared by dissolving 1 g of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) and 380 mg of p-tolyenesulfonic acid in 4 ml of anhydrous ethanol contained in a vial. Into this solution was added 30 ml of anhydrous diethyl ether. The mixture was titrated with additional drops of ethanol until it was clear. The vial containing the mixture was covered (with a vented covering) and left to stand quiescent under ambient conditions for 48 hours during which time crystals of the tosylate form I salt of the compound of Formula I precipitated. The precipitated crystals were isolate by filtration, washed with an aliquot of diethyl ether and dried in air. The crystals were subsequently collected and dried under house vacuum overnight.

With reference to FIGS. 9 to 11 and 19, the tosylate form I salt form of the compound of Formula I thus obtained was characterized by X-ray Powder Diffraction, Infrared, and Raman spectroscopic techniques and by DSC, as in accordance with the procedures described above. Table XVII, below, lists 12 characteristic peaks of the X-ray Powder Diffraction spectrum shown in FIG. 9, expressed in diffraction angle expressed in degrees 2 theta (°2θ) values are shown as +/−0.02 (°2θ)), the corresponding "d" spacing in angstroms (A), shown +/−0.04 A, and relative intensities of the signal ("RI") in the following notation: S=strong, M=medium, W=weak; B=Broad, V=Very and D=diffuse:

TABLE XVII

| Diffraction Angle (°2 θ, ±0.2) | d spacing (A, ±0.04) | relative intensity |
| --- | --- | --- |
| 9.4 | 9.36 | M |
| 9.9 | 8.91 | W |
| 12.8 | 6.92 | M |
| 14.4 | 6.14 | W |
| 15.1 | 5.86 | M |
| 18.0 | 4.93 | M |
| 20.0 | 4.43 | S |
| 21.0 | 4.22 | S |
| 21.7 | 4.09 | S |
| 23.5 | 3.78 | M |
| 25.3 | 3.51 | S |
| 28.5 | 3.13 | M |

Of the peaks characteristic of the the tosylate form I salt form of the compound of Formula I shown in Table XVII, the eight most characteristic peaks are those appearing at diffraction angles (in °2θ) equal to 9.4, 12.8, 15.1, 18.0, 20.0, 21.0, 21.7, and 25.3, and the four most characteristic peaks are those appearing at diffraction angles (in °2Θ) equal to 9.4, 20.0, 21.0, and 25.3.

Figure 10:
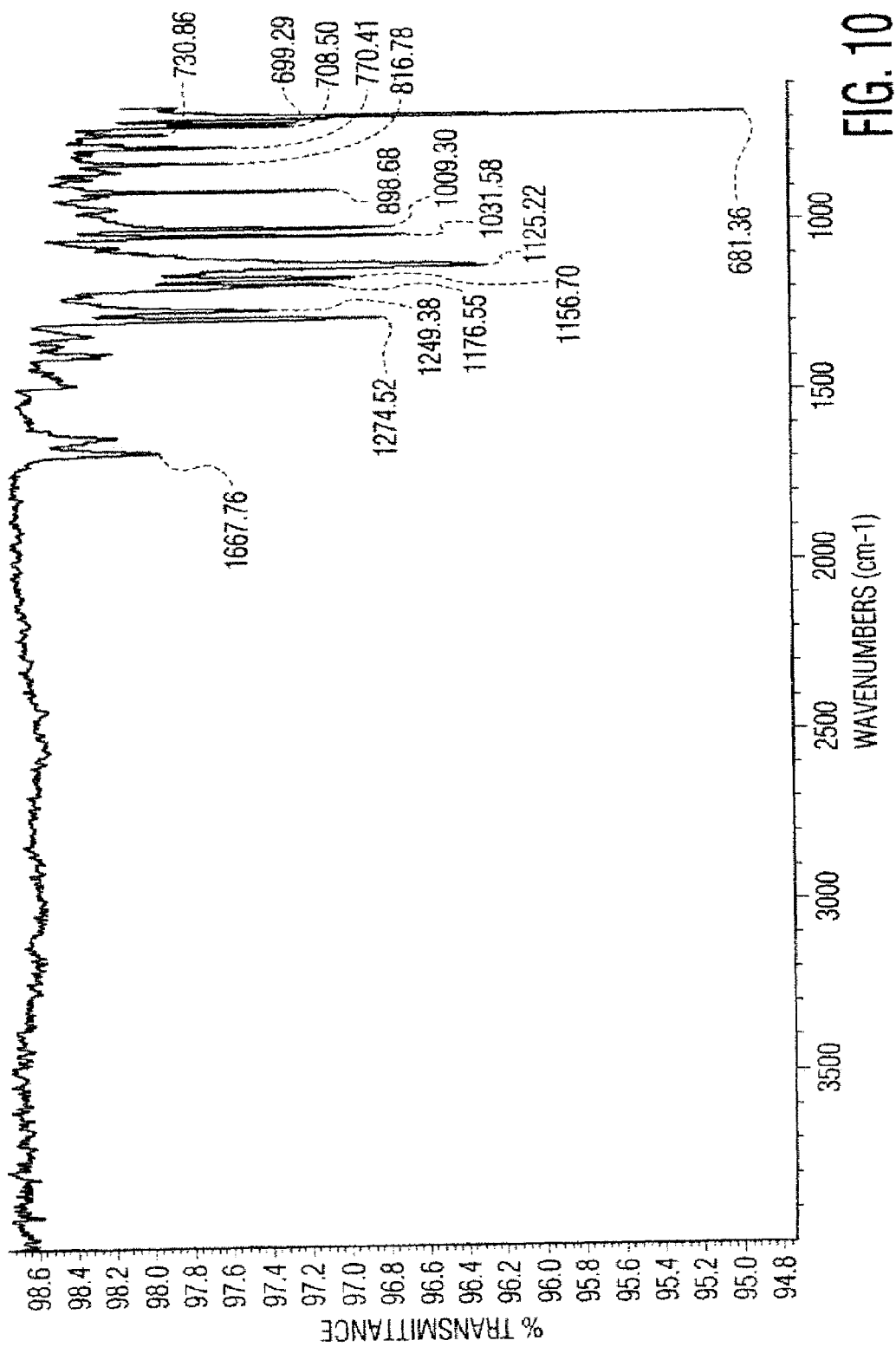
FIG. 10 presents a characteristic infrared spectrum of the crystalline tosylate salt form I of the compound of Formula I [Vertical Axis; Transmittance (Percent); Horizontal Axis: wavenumber (cm−1)].

FIG. 10 illustrates a transmission infrared spectrum of the tosylate form I salt form of the compound of Formula I obtained utilizing the procedure described above. Table XVIII, below, lists the 12 most characteristic peaks of the crystalline tosylate form I salt, and in an adjacent column, the relative absorption intensity of each listed peak is identified utilizing the notation: S=Strong, M=Moderate, W=Weak, V=Very.

TABLE XVIII

| Absorption Peak | Wave No. (cm$^{-1}$) | relative intensity |
| --- | --- | --- |
| 1 | 1668 | M |
| 2 | 1275 | S |
| 3 | 1249 | M |
| 4 | 1177 | M |
| 5 | 1157 | S |
| 6 | 1125 | S |
| 7 | 1032 | S |
| 8 | 1009 | S |
| 9 | 899 | M |
| 10 | 817 | M |
| 11 | 770 | M |
| 12 | 681 | S |

Of the characteristic peaks shown in Table XVIII, the 8 most characteristic peaks of the compound are those appearing at 1668, 1275, 1157, 1125, 1032, 1009, 899, and 681 reciprocal centimeters (cm$^{-1}$), and the four most characteristic peaks are those appearing at 1275, 1125, 1032, and 681 cm$^{-1}$.

Figure 11:
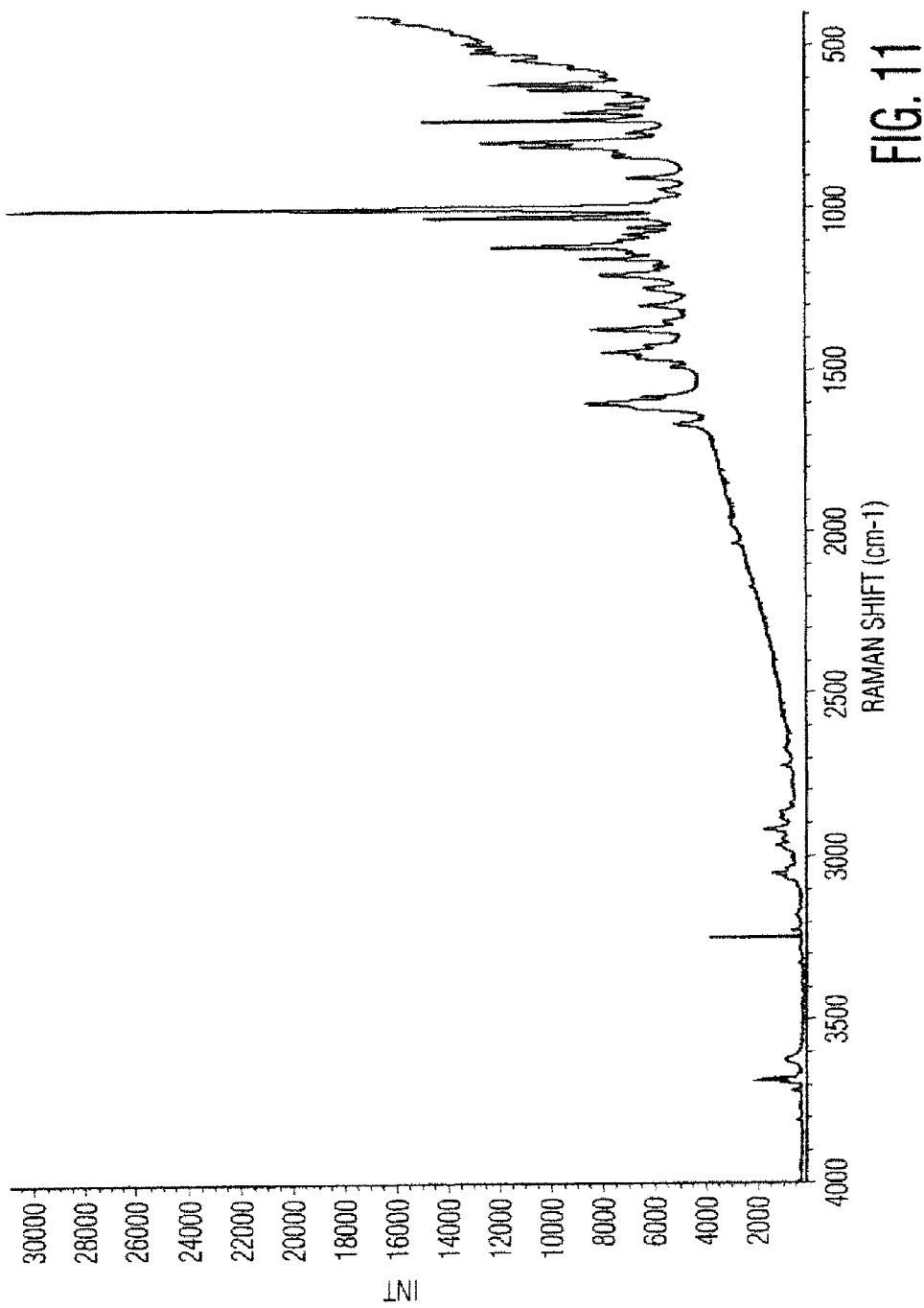
FIG. 11 presents a characteristic Raman spectrum of the crystalline tosylate salt form I of the compound of Formula I, [horizontal axis; Raman shift in reciprocal centimeters, vertical axis; relative intensity versus background].

FIG. 11 illustrates a Raman spectrum of the tosylate form I salt form of the compound of Formula I. Table XIX, below, lists the 12 most characteristic scattering peaks of the compound (in reciprocal centimeters, (cm$^{-1}$)). Listed in an adjacent column beside each peak listed in Table XI, the relative absorption intensity of each peak is indicated in the notation: S=Strong; M=Moderate; W=Weak; V=Very; B=Broad.

TABLE XIX

| Scattering Peak | Wave No. (cm$^{-1}$) | relative intensity |
| --- | --- | --- |
| 1 | 3695 | W |
| 2 | 3690 | W |
| 3 | 3250 | M |
| 4 | 1602 | MB |
| 5 | 1371 | W |
| 6 | 1117 | W |
| 7 | 1026 | M |
| 8 | 996 | S |
| 9 | 793 | MB |
| 10 | 727 | VW |
| 11 | 632 | M |
| 12 | 615 | VW |

Of the characteristic peaks shown in Table XIX, the 8 most characteristic peaks of the compound are those appearing at 3695, 3250, 1117, 1026, 996, 793, 727, and 615 cm$^{-1}$, and the four most characteristic peaks are those appearing at 3250, 1117, 996, and 727 cm$^{-1}$.

Figure 19:
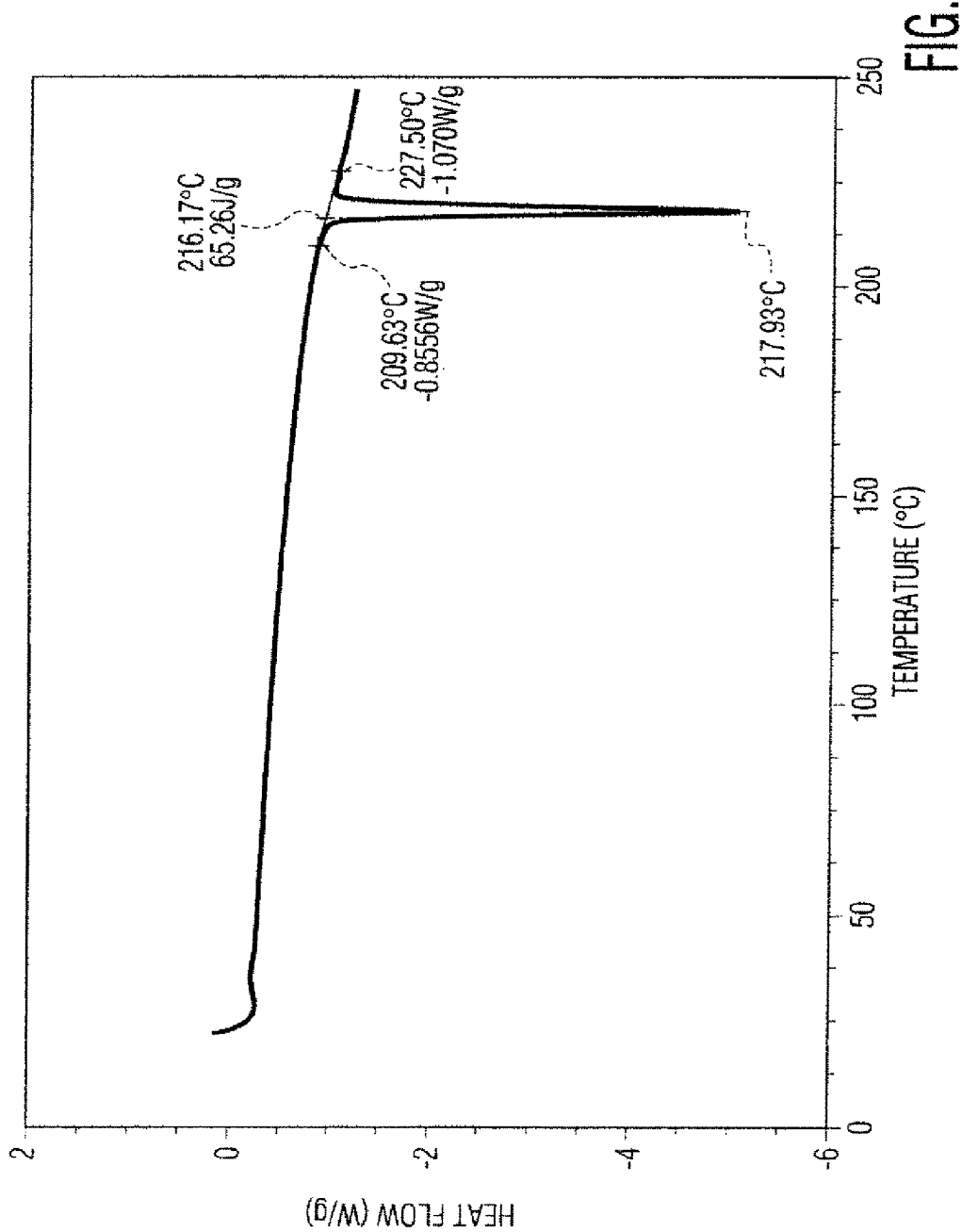
FIG. 19 presents a characteristic differential scanning calorimetry thermogram of the crystalline tosylate salt form I of the compound of Formula I, [Vertical Axis; Heat Flow in cal/sec/g; Horizontal Axis: Temperature in degrees centigrade].

The crystalline tosylate form I salt form of the compound of Formula I was analyzed by differential scanning calorimetry using the procedure described above. FIG. 19 illustrates the DSC thermogram thereby obtained. The DSC thermogram contains a single sharp endotherm centered at approximately 218° C., which is the melting point of the crystalline tosylate form I salt form of the compound of Formula I.

When examined for solubility in accordance with the above-described procedure, it was found that the tosylate form I salt of the compound of Formula I has aqueous solubility, at pH of 4 or less (more acidic), of at least 0.38 mg/ml, and had the following solubilities at ambient temperatures in the pharmaceutical solvents shown below in Table XX.

TABLE XX

| Solvent | Solubility (mg/ml, ambient conditions) |
| --- | --- |
| Ethanol | 75 |
| Propylene Glycol | 20 |
| PEG 400 ™ | 1.8 |
| Glycerin | 2.5 |

The stability of the crystalline tosylate form I salt form of the compound of Formula I was examined by placing weighed amounts of the salt into clear glass vials and storing them under the indicated conditions. Periodically a vial was removed and the contents examined for decomposition of the compound. Accordingly, samples of the tosylate form I salt were exposed to the following conditions: (a) 40° C. and 75% relative humidity (RH) for four weeks; (b) 50° C. and ambient relative humidity for four weeks; and (c) 70° C. for one hour. Samples of the tosylate form I salt were separately tested for one cycle of ICH UV/Vis light stress conditions. These tests illustrate that the crystalline tosylate form I salt form of the compound of Formula I is stable under all tested conditions.

Tosylate Form II Salt

Figure 12:
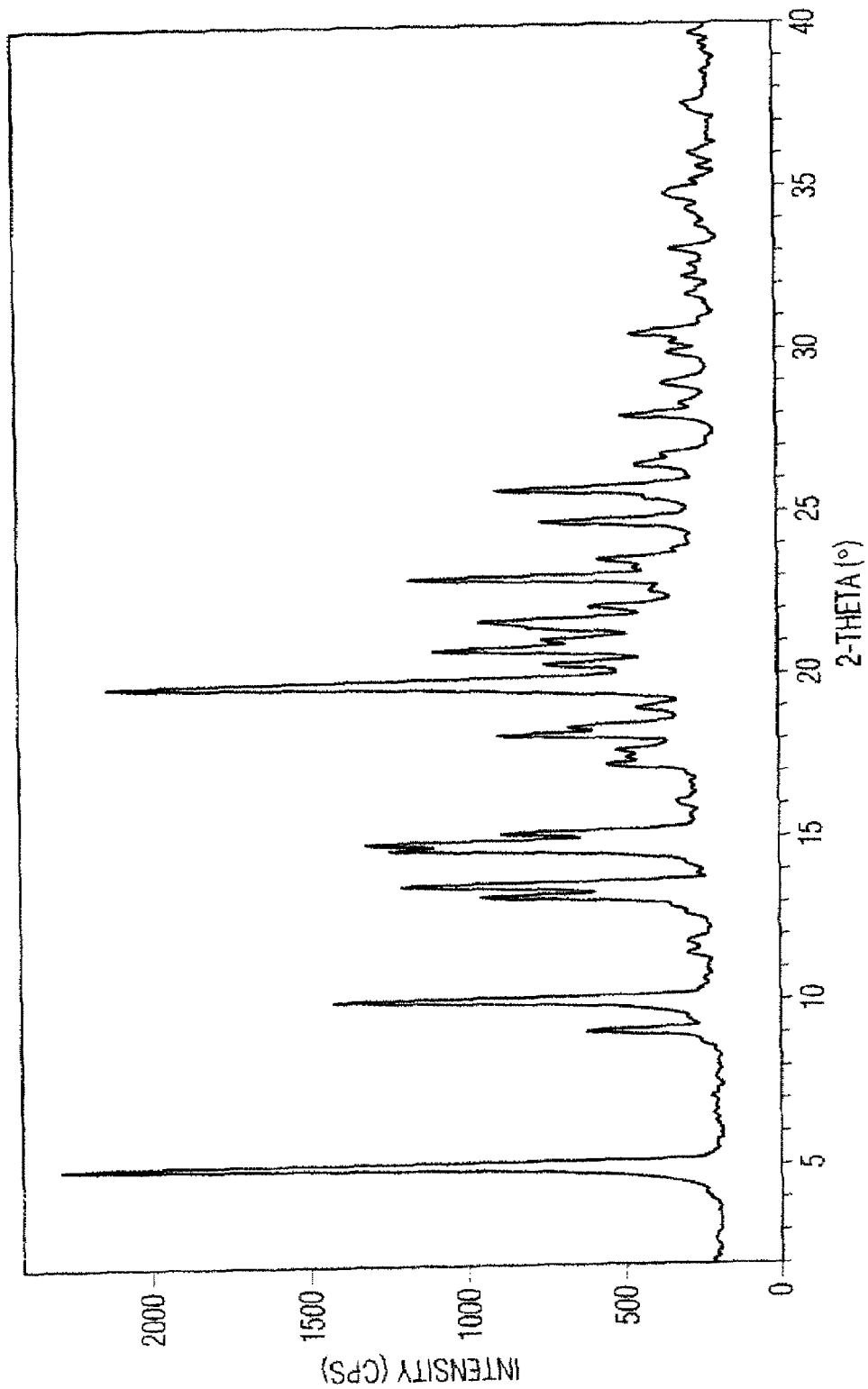
FIG. 12 presents a characteristic x-ray powder diffraction pattern of the crystalline tosylate salt form II (crystallized from acetonitrile) of the compound of Formula I, [Vertical Axis: Intensity (CPS, counts (square root)); Horizontal Axis: Two Theta ((2θ) degrees)].
Figure 15:
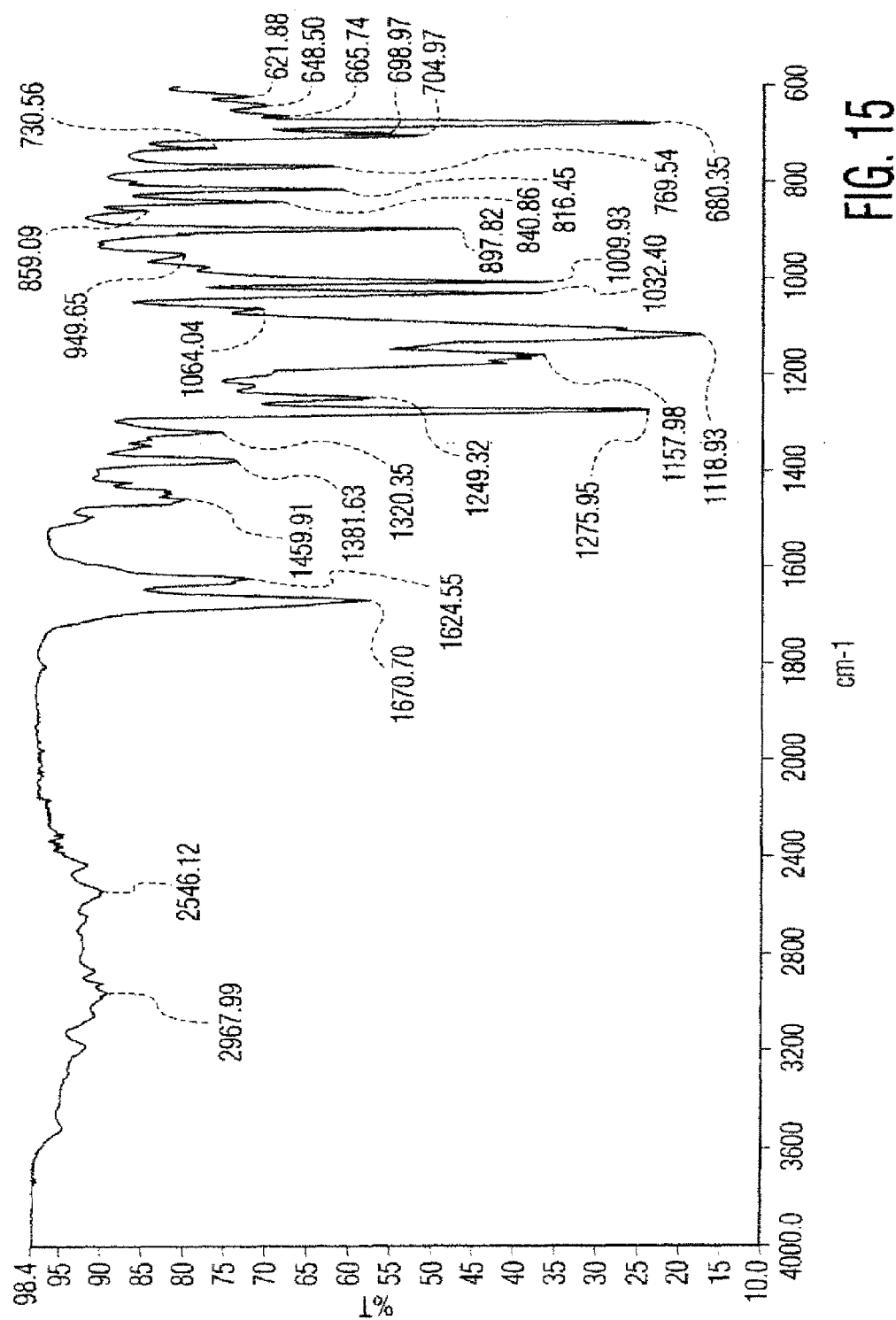
FIG. 15 presents a characteristic infrared spectrum of the crystalline tosylate salt form II (crystallized from acetonitrile) of the compound of Formula I [Vertical Axis; Transmittance (Percent); Horizontal Axis: wavenumber (cm−1)].
Figure 16:
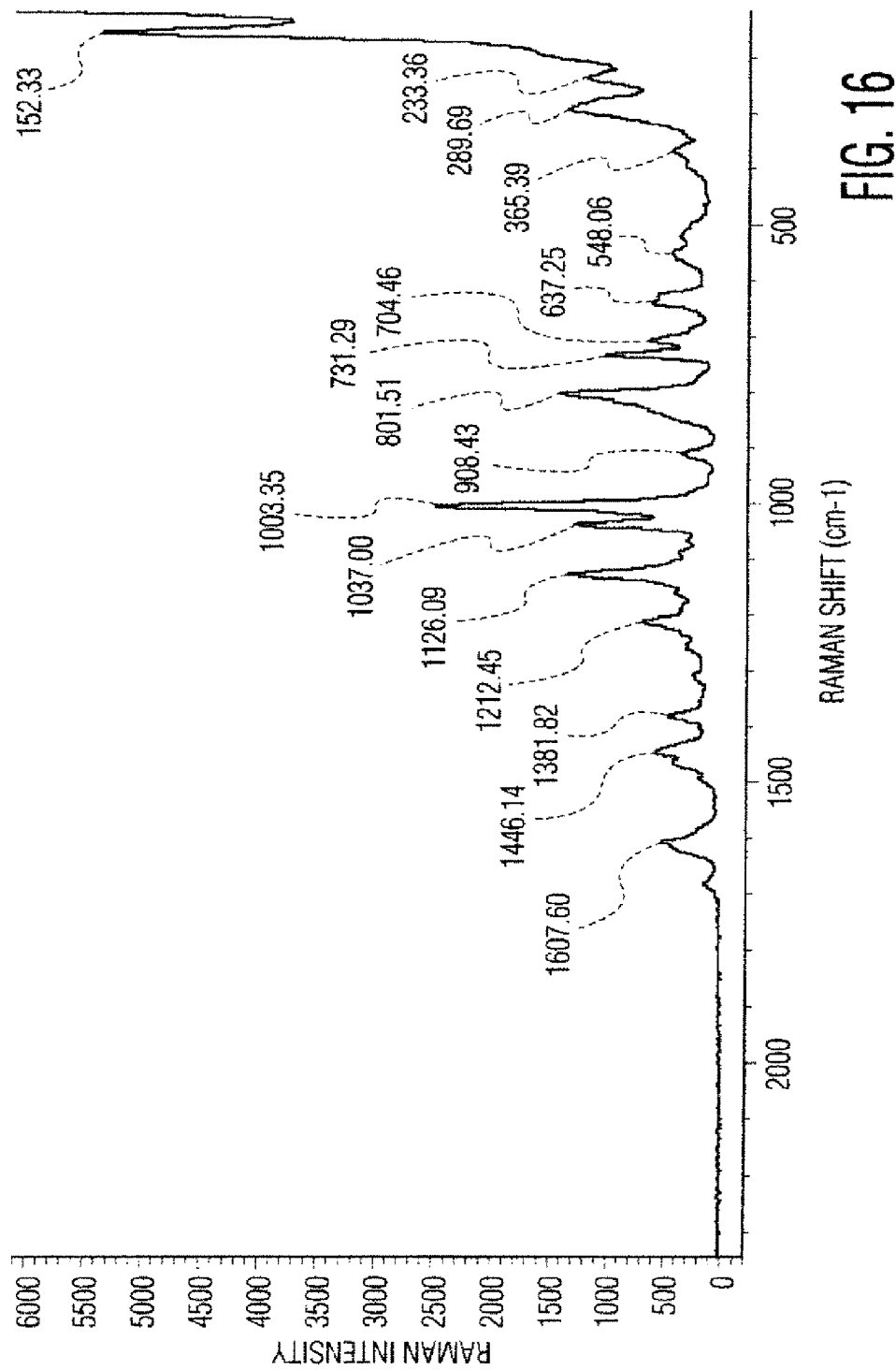
FIG. 16 presents a characteristic Raman spectrum of the crystalline tosylate salt form II (crystallized from acetonitrile) of the compound of Formula I, [horizontal axis, Raman shift in reciprocal centimeters, vertical axis; relative intensity versus background].

Utilizing the general slurry procedures described herein, tosylate form II salt of (5S,8S)-8-[{(1R)-1-(3,5-Bis-(trifuoromethyl)phenyl)-ethoxy}-methyl]-8-phenyl-1,7-diazaspiro[4.5]decan-2-one (the tosylate form II salt of the compound of Formula I) was prepared by slurrying in acetonitrile (ACN) the crystalline tosylate form I salt prepared in accordance with the procedure described above. With reference to FIGS. 12, 15 and 16, the crystalline tosylate form II salt form of the compound of Formula I was characterized by X-ray Powder Diffraction, Infrared, and Raman spectroscopies and analyzed by DSC.

FIG. 12 shows the X-ray Powder Diffraction Spectrum of the crystalline tosylate form II salt form of the compound of Formula I, obtained using the general procedure described herein. Table XXI, below, lists 12 characteristic peaks of the X-ray Powder Diffraction spectrum shown in FIG. 12. Table XXI lists the characteristic peaks by diffraction angle expressed in degrees 2 theta (°2Θ), the corresponding "d" spacing in angstroms (A), and relative intensities of the signal ("RI") in the following notation: S=strong; M=medium=W=weak; B=Broad, V=Very and D=diffuse:

TABLE XXI

| Diffraction Angle (°2 Θ, ±0.2) | d spacing (A, ±0.04) | relative intensity |
|---|---|---|
| 5.0 | 17.66 | S |
| 9.1 | 9.73 | W |
| 10.0 | 8.80 | S |
| 13.2 | 6.70 | M |
| 13.6 | 6.52 | M |
| 14.9 | 5.96 | M |
| 15.0 | 5.85 | S |
| 18.2 | 4.88 | M |
| 19.7 | 4.49 | S |
| 23.0 | 3.87 | M |
| 24.7 | 3.60 | M |
| 25.7 | 3.46 | M |

Of the peaks shown in Table XXI characteristic of the crystalline tosylate form II salt form of the compound of Formula I, the eight most characteristic peaks are those appearing at diffraction angles (in °2θ) equal to 5.0, 9.1, 10.0, 13.2, 13.6, 14.9, 19.7 and 23.0, and the four most characteristic peaks are those appearing at diffraction angles (in °2θ) equal to 5.0, 10.0, 13.6, and 19.7.

FIG. 15 illustrates a transmission infrared spectrum of the crystalline tosylate form II salt form of the compound of Formula I, obtained using the procedure described above. Table XXII, below, lists the 12 most characteristic peaks of the spectrum of crystalline tosylate form II salt shown in FIG. 15, and in an adjacent column beside each of the listed peaks, represents the relative absorption intensity of each listed peak utilizing the notation: S=Strong, M=Moderate, W=Weak, B=Broad, V=Very.

TABLE XXII

| Absorption Peak | Wave No. (cm$^{-1}$) | relative intensity |
|---|---|---|
| 1 | 1671 | MB |
| 2 | 1625 | MB |
| 3 | 1276 | S |
| 4 | 1158 | MB |
| 5 | 1119 | SB |

TABLE XXII-continued

| Absorption Peak | Wave No. (cm$^{-1}$) | relative intensity |
|---|---|---|
| 6 | 1032 | S |
| 7 | 1010 | S |
| 8 | 898 | S |
| 9 | 816 | M |
| 10 | 770 | M |
| 11 | 705 | M |
| 12 | 680 | S |

Of the characteristic peaks shown in Table XXII, the 8 most characteristic peaks of the compound are those appearing at 1671, 1625, 1276, 1158, 1119, 1032, 1010, 898, 816, 770, 705, and 680 reciprocal centimeters (cm$^{-1}$), and the four most characteristic peaks are those appearing at 1671, 1276, 1119, and 680 cm$^{-1}$.

FIG. 16 illustrates a Raman spectrum of the crystalline tosylate form II salt form of the compound of Formula I obtained using the procedure described above. Table XXIII lists the 12 most characteristic scattering peaks shown in FIG. 16 (in reciprocal centimeters, cm$^{-1}$). In a column adjacent to the listed peaks, Table XXIII represents the relative absorption intensity of each peak in the notation: S=Strong; M=Moderate; W=Weak; V=Very; B=Broad.

TABLE XXIII

| Scattering Peak | Wave No. (cm$^{-1}$) | relative intensity |
|---|---|---|
| 1 | 1608 | WB |
| 2 | 1446 | WB |
| 3 | 1212 | WB |
| 4 | 1126 | M |
| 5 | 1037 | M |
| 6 | 1003 | M |
| 7 | 802 | MB |
| 8 | 731 | WB |
| 9 | 637 | WB |
| 10 | 290 | WB |
| 11 | 233 | VWB |
| 12 | 152 | S |

Of the characteristic peaks shown in Table XXIII, the 8 most characteristic peaks of the compound are those appearing at 1608, 1126, 1037, 1003, 802, 731, 290, 152 cm$^{-1}$, and the four most characteristic peaks are those appearing at 1126, 1037, 1003, and 802 cm$^{-1}$.

Figure 20:
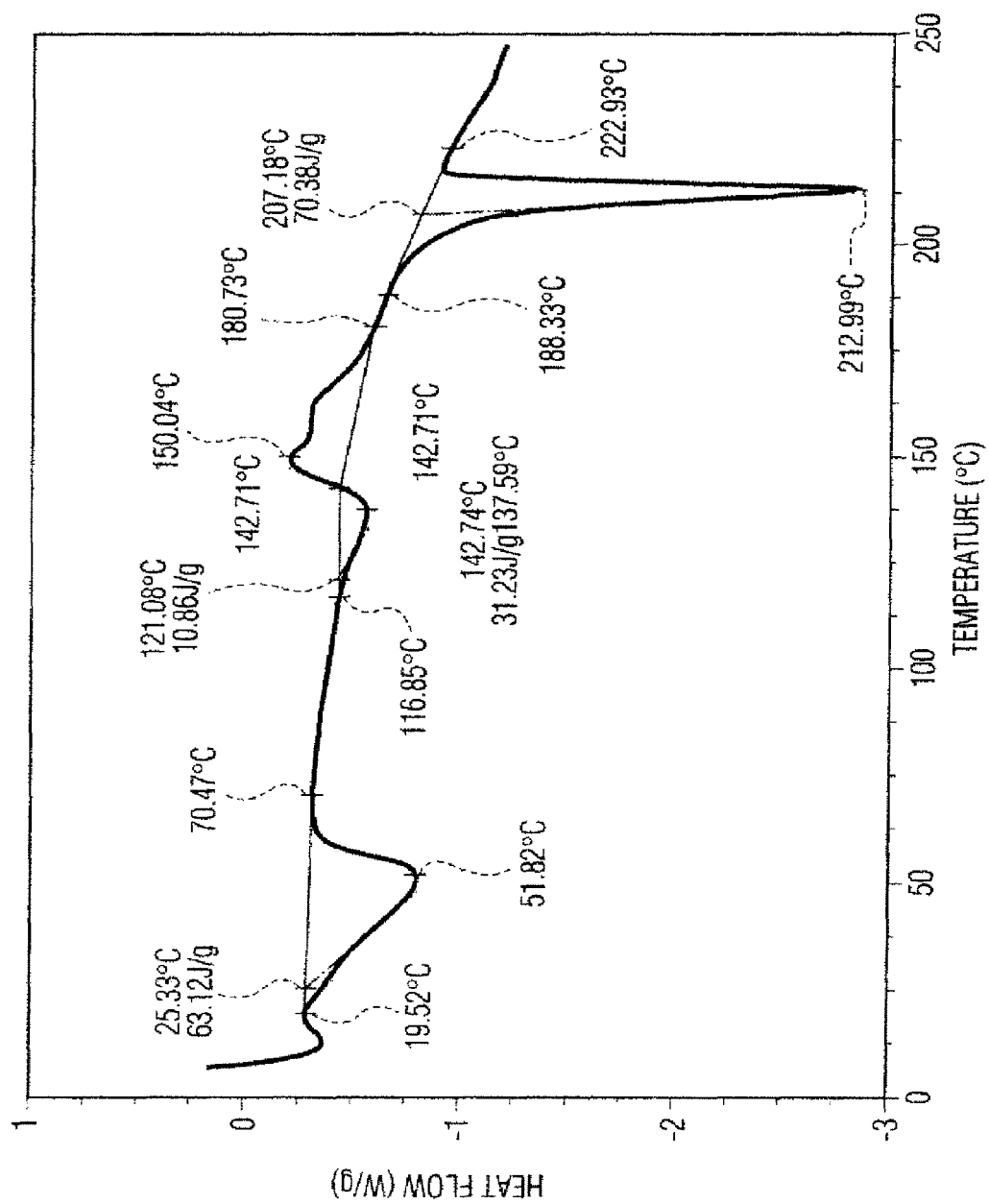
FIG. 20 presents a characteristic differential scanning calorimetry thermogram of the crystalline tosylate salt form II (crystallized from acetonitrile) of the compound of Formula I, [Vertical Axis; Heat Flow in cal/sec/g; Horizontal Axis: Temperature in degrees centigrade].

The crystalline tosylate form II salt form of the compound of Formula I was analyzed also by differential scanning calorimetry, using the general procedure described above. The DSC thermogram thus obtained is shown in FIG. 20. With reference to FIG. 20, the DSC thermogram contains two broad endotherms, one centered at approximately 52° C., which is attributable to loss of solvent of crystallization. The second broad endotherm, centered at about 143° C., is attributable to melting and decomposition of the salt form remaining after driving off the solvent.

Tosylate Form III Salt

Figure 13:
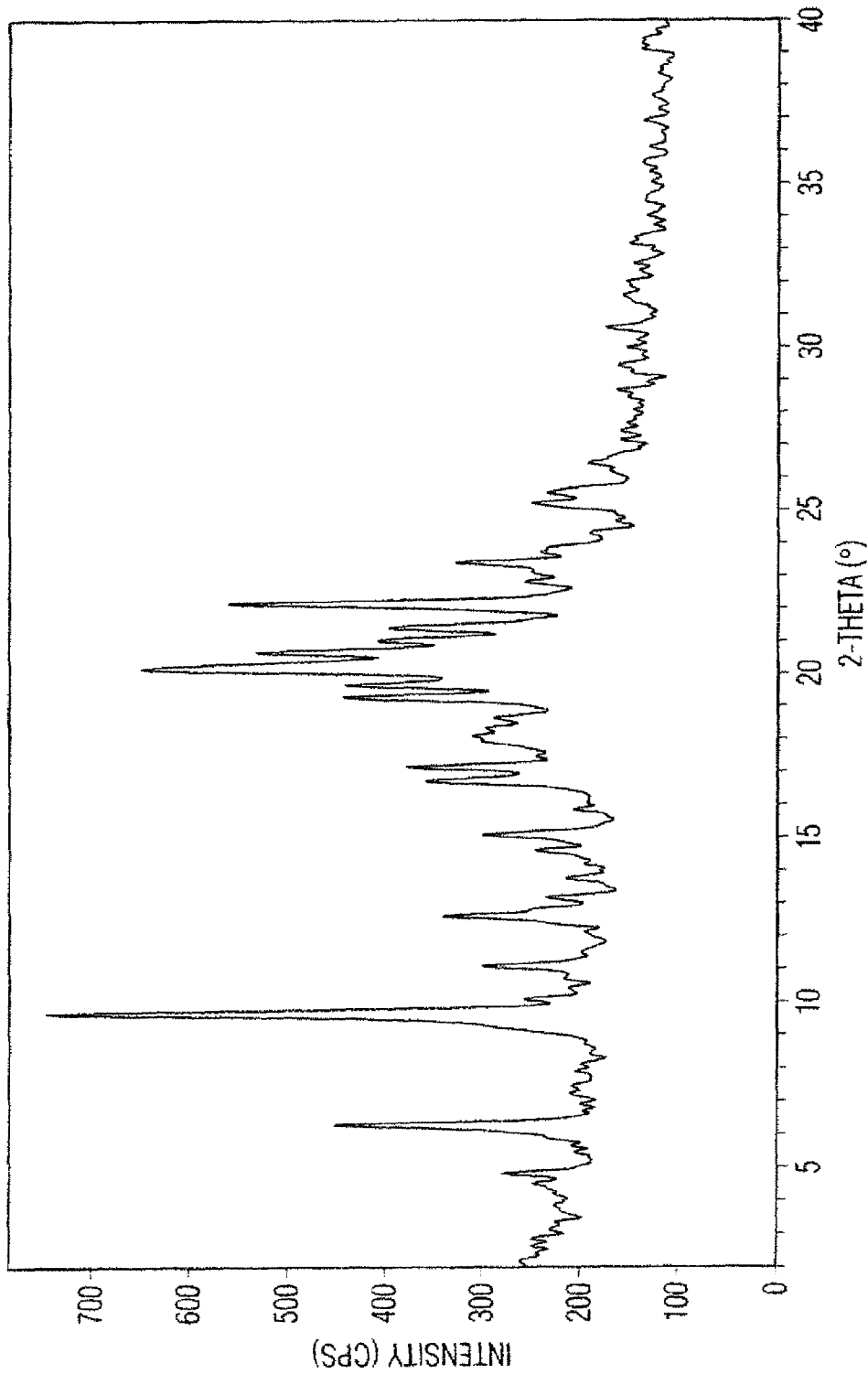
FIG. 13 presents a characteristic x-ray powder diffraction pattern of the crystalline tosylate salt form III (hexane solvate) of the compound of Formula I, [Vertical Axis: Intensity (CPS, counts (square root)); Horizontal Axis: Two Theta ((2θ) degrees)].
Figure 21:
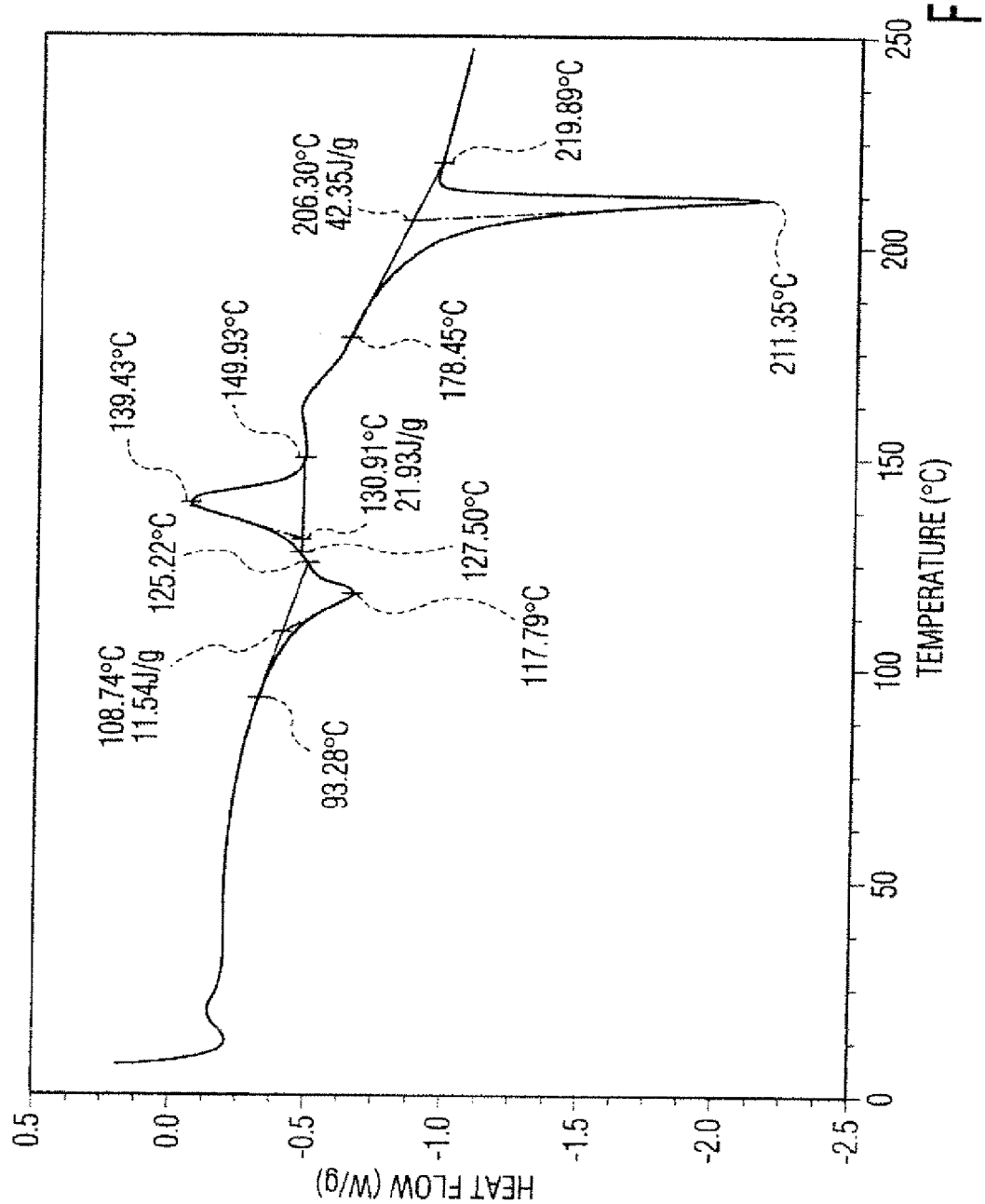
FIG. 21 presents a characteristic differential scanning calorimetry thermogram of the crystalline tosylate salt form III (hexane solvate) of the compound of Formula I, [Vertical Axis; Heat Flow in cal/sec/g; Horizontal Axis: Temperature in degrees centigrade].

Using the general slurrying procedure described herein, the Tosylate salt form III of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) was prepared by slurrying in hexane the crystalline tosylate salt form I prepared as described above. With reference to FIGS. 13 and 21, the crystalline tosylate form III salt form of the compound of Formula I was characterized by X-ray Powder Diffraction spectroscopy and analyzed by DSC using the above-described procedures.

Table XXIV, below, lists 12 characteristic peaks of the X-ray Powder Diffraction spectrum shown in FIG. 13, expressed in diffraction angle expressed in degrees 2 theta (°2θ), the corresponding "d" spacing in angstroms (A), and relative intensities of the signal ("RI") in the following notation: S=strong, M=medium, B=Broad, W=weak; V=Very and D=diffuse:

TABLE XXIV

| Diffraction Angle (°2 θ, ±0.2) | d spacing (A, ±0.04) | relative intensity |
|---|---|---|
| 6.3 | 14.02 | M |
| 9.7 | 9.13 | S |
| 11.1 | 7.95 | W |
| 12.6 | 6.70 | WB |
| 15.1 | 5.85 | WB |
| 16.7 | 5.29 | M |
| 17.2 | 5.16 | M |
| 19.3 | 4.59 | M |
| 20.2 | 4.39 | SB |
| 20.7 | 4.29 | SB |
| 22.2 | 4.00 | S |
| 23.4 | 3.79 | WB |

Of the peaks shown in Table XXIV characteristic of the crystalline tosylate form III salt form of the compound of Formula I, the eight most characteristic peaks are those appearing at diffraction angles (in °2θ) equal to 6.3, 9.7, 12.6, 16.7, 17.2, 20.2, 20.7, and 22.2, and the four most characteristic peaks are those appearing at diffraction angles (in °2Θ) equal to 6.3, 9.7, 20.2, and 22.2.

FIG. 21 illustrates the DSC thermogram obtained from DSC analysis of the crystalline tosylate form III salt form of the compound of Formula I, obtained using the procedure described above. The DSC thermogram contains a broad endotherm centered at approximately 130° C., which is attributable to loss of solvent of crystallization and decomposition of the crystalline material remaining after solvent loss.

Tosylate Form IV Salt

Figure 14:
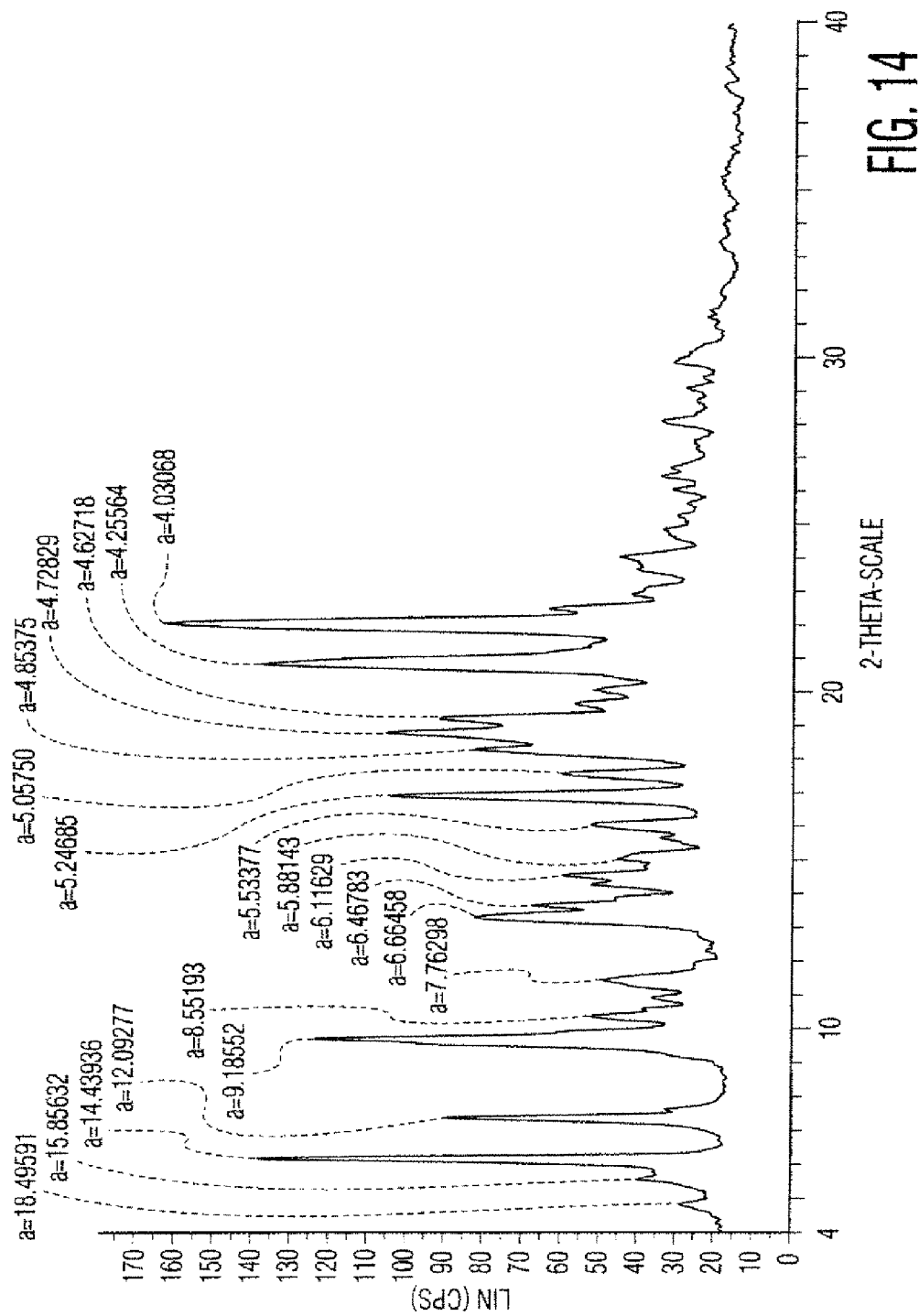
FIG. 14 presents a characteristic x-ray powder diffraction pattern of the crystalline tosylate salt form IV (THF solvate) of the compound of Formula I, [Vertical Axis: Intensity (CPS, counts (square root)); Horizontal Axis: Two Theta ((2θ) degrees)].
Figure 17:
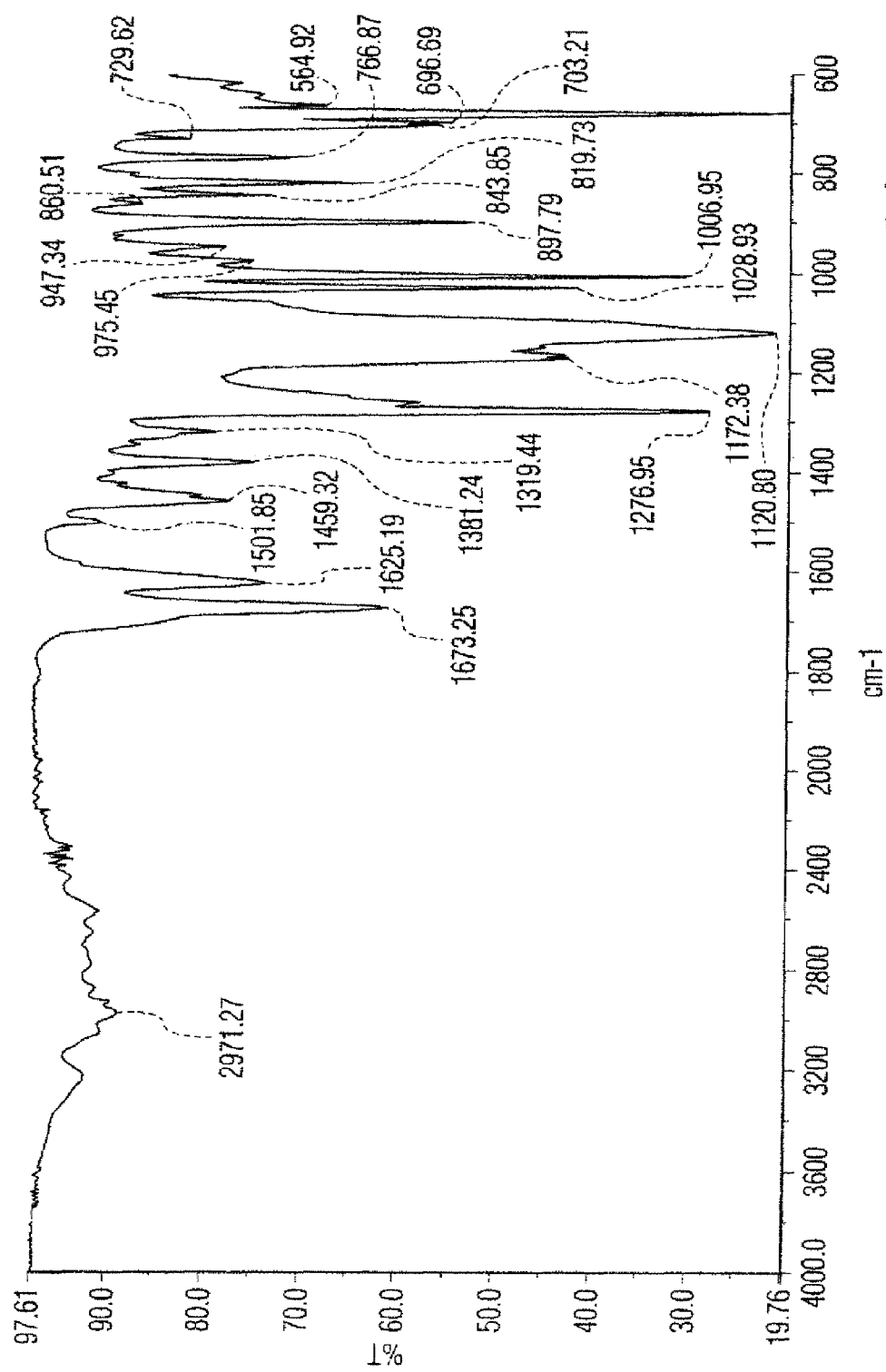
FIG. 17 presents a characteristic infrared spectrum of the crystalline tosylate salt form IV (THF solvate) of the compound of Formula I [Vertical Axis; Transmittance(Percent); Horizontal Axis: wavenumber (cm−1)].
Figure 18:
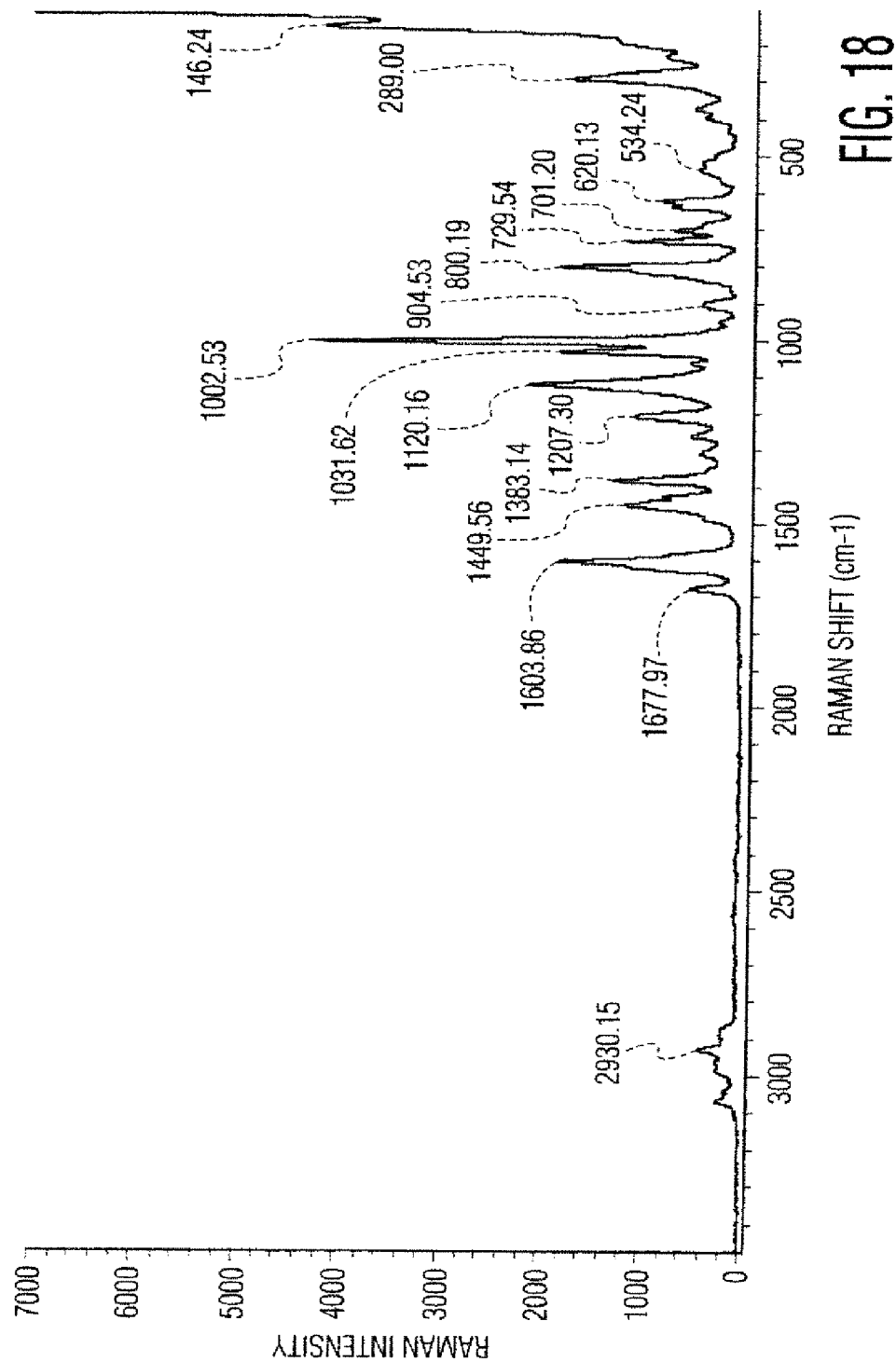
FIG. 18 presents a characteristic Raman spectrum of the crystalline tosylate salt form IV (THF solvate) of the compound of Formula I, [horizontal axis; Raman shift in reciprocal centimeters, vertical axis; relative intensity versus background]

Utilizing the general slurrying procedure described herein, tosylate salt form IV of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) was prepared by slurrying in tetrahydrofuran (THF) the crystalline tosylate form I salt prepared as described above to provide the THF solvate. With reference to FIGS. 14, 17 and 18, the crystalline tosylate form IV salt form of the compound of Formula I was characterized by X-ray Powder Diffraction, Infrared, and Raman spectroscopies.

FIG. 14 illustrates an X-ray Powder Diffraction Spectrum of the crystalline tosylate form IV salt form of the compound of Formula I obtained using the general procedure described herein. Table XXV, below, lists 12 characteristic peaks of the X-ray Powder Diffraction spectrum shown in FIG. 14, expressed in diffraction angle expressed in degrees 2 theta (°2θ), the corresponding "d" spacing in angstroms (A), and relative intensities of the signal ("RI") in the following notation: S=strong, M=medium, B=Broad, W=weak, V=Very and D=diffuse.

TABLE XXV

| Diffraction Angle (°2 θ, ±0.2) | d spacing (A, ±0.04) | relative intensity |
|---|---|---|
| 6.1 | 14.44 | S |
| 7.3 | 12.09 | M |
| 9.6 | 9.19 | S |
| 11.4 | 7.76 | MB |
| 13.3 | 6.66 | M |
| 16.0 | 5.53 | M |
| 16.9 | 5.25 | S |
| 17.5 | 5.06 | M |
| 18.8 | 4.73 | MB |
| 19.2 | 4.63 | SB |
| 20.9 | 4.26 | S |
| 22.2 | 4.03 | S |

Of the peaks shown in Table XXV characteristic of the crystalline tosylate form II salt form of the compound of Formula I, the eight most characteristic peaks are those appearing at diffraction angles (in °2θ) equal to 6.1, 7.3, 9.6, 13.3, 16.9, 18.8, 20.9 and 22.0, and the four most characteristic peaks are those appearing at diffraction angles (in °2θ) equal to 6.1, 9.6, 20.9 and 22.0.

FIG. 17 illustrates a transmission infrared spectrum of the crystalline tosylate form IV salt form of the compound of Formula I obtained using the procedure described herein. Table XXVI, below, lists the 12 most characteristic peaks of the crystalline tosylate form IV salt and in an adjacent column represents the relative absorption intensity of each listed peak utilizing the notation: S=Strong, M=Moderate, W=Weak, B=Broad, V=Very.

TABLE XXVI

| Absorption Peak | Wave No. (cm$^{-1}$) | relative intensity |
|---|---|---|
| 1 | 1673 | MB |
| 2 | 1459 | MB |
| 3 | 1381 | S |
| 4 | 1277 | MB |
| 5 | 1172 | SB |
| 6 | 1121 | S |
| 7 | 1029 | S |
| 8 | 1007 | S |
| 9 | 898 | M |
| 10 | 820 | M |
| 11 | 767 | M |
| 12 | 665 | S |

Of the characteristic peaks shown in Table XXVI, the 8 most characteristic peaks of the compound are those appearing at 1673, 1277, 1172, 1121, 1029, 1007, 898, and 665 reciprocal centimeters (cm$^{-1}$), and the four most characteristic peaks are those appearing at 1277, 1121, 1007, and 665 cm$^{-1}$.

FIG. 18 illustrates a Raman spectrum of the crystalline tosylate form IV salt form of the compound of Formula I obtained using the procedure described above.

Table XXVII lists the 12 most characteristic scattering peaks in the Raman spectra shown in FIG. 18, and in an adjacent column represents the intensity of each listed peak in the notation: S=Strong; M=Moderate; W=Weak; V=Very; B=Broad.

TABLE XXVII

| Scattering Peak | Wave No. (cm$^{-1}$) | relative intensity |
|---|---|---|
| 1 | 1678 | W |
| 2 | 1604 | M |
| 3 | 1450 | MB |
| 4 | 1383 | M |

TABLE XXVII-continued

| Scattering Peak | Wave No. (cm$^{-1}$) | relative intensity |
|---|---|---|
| 5 | 1207 | M |
| 6 | 1120 | M |
| 7 | 1003 | S |
| 8 | 800 | M |
| 9 | 730 | W |
| 10 | 620 | WB |
| 11 | 289 | M |
| 12 | 146 | S |

Of the characteristic peaks shown in Table XXVII, the 8 most characteristic peaks of the compound are those appearing at 1604, 1450, 1383, 1207, 1120, 1003, 800, and 289 cm$^{-1}$, and the four most characteristic peaks are those appearing at 1604, 1003, 800, and 289 cm$^{-1}$.

What is claimed is:

1. A method of treating or delaying the onset of chemotherapy-induced nausea and/or chemotherapy-induced emesis in a mammal receiving chemotherapy which comprises administering to said mammal a medicament comprising a therapeutically effective amount of a crystalline Form I monohydrate hydrochloride salt form of the compound (5S,8S)-8-[{(1R)-1-(3,5-Bis-(trifluoromethyl)phenyl)-ethoxy}-methyl]-8-phenyl-1,7-diazaspiro[4,5]decan-2-one (Formula I):

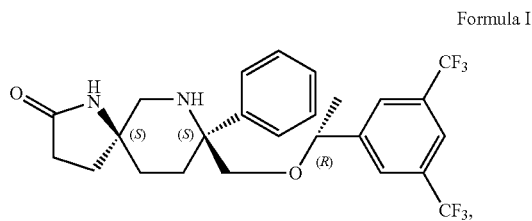

Formula I wherein the crystalline Form I monohydrate hydrochloride salt form is characterized by an x-ray powder diffraction pattern including at least a strong peak having a diffraction angle (in 2θ) of 21.6±0.2 and lattice spacing (in Å) of 4.11±0.04.

2. The method of claim 1 further comprising administering said medicament in combination with a therapeutically effective amount of a chemotherapeutic agent.

3. The method of claim 2 wherein said chemotherapeutic agent is temozolomide.

4. The method of claim 1, wherein one or more additional therapeutic agents are administered in combination with the crystalline Form I monohydrate hydrochloride salt form of the compound (5S,8S)-8-[{(1R)-1-(3,5-Bis-(trifluoromethyl)phenyl)-ethoxy}-methyl]-8-phenyl-1,7-diazaspiro[4,5]decan-2-one.

5. The method of claim 1 further comprising contemporaneous administration of a chemotherapeutic agent.

6. The method of claim 5 wherein the chemotherapeutic agent is temozolomide.

7. The method of claim 1, wherein the crystalline Form I monohydrate hydrochloride salt form of (5S,8S)-8-[{(1R)-1-(3,5-Bis-(trifluoromethyl)phenyl)-ethoxy}-methyl]-8-phenyl-1,7-diazaspiro[4,5]decan-2-one is characterized by an x-ray powder diffraction pattern having at least one additional peak selected from

| Diffraction angle (2Θ ± 0.2) | RI | Lattice Spacing (Å ± 0.04) |
|---|---|---|
| 16.1 | Medium | 5.49 |
| 18.4 | Medium | 4.83 |
| 23.5 | Medium | 3.78 |

8. The method of claim 1, wherein the crystalline Form I monohydrate hydrochloride salt form of (5S,8S)-8-[{(1R)-1-(3,5-Bis-(trifluoromethyl)phenyl)-ethoxy}-methyl]-8-phenyl-1,7-diazaspiro[4,5]decan-2-one is characterized by an x-ray powder diffraction pattern having at least two additional peaks selected from

| Diffraction angle (2Θ ± 0.2) | RI | Lattice Spacing (Å ± 0.04) |
|---|---|---|
| 16.1 | Medium | 5.49 |
| 18.4 | Medium | 4.83 |
| 23.5 | Medium | 3.78 |

9. The method of claim 1, wherein the crystalline Form I monohydrate hydrochloride salt form of (5S,8S)-8-[{(1R)-1-(3,5-Bis-(trifluoromethyl)phenyl)-ethoxy}-methyl]-8-phenyl-1,7-diazaspiro[4,5]decan-2-one is characterized by an x-ray powder diffraction pattern which includes the following peaks:

| Diffraction angle (2Θ ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Medium | 3.78 |

10. A method of treating or delaying the onset of nausea and/or emesis in a mammal which comprises administering to said mammal a medicament comprising a therapeutically effective amount of a crystalline Form I monohydrate hydrochloride salt form of the compound (5S,8S)-8-[{(1R)-1-(3,5-Bis-(trifluoromethyl)phenyl)-ethoxy}-methyl]-8-phenyl-1,7-diazaspiro[4,5]decan-2-one (formula I):

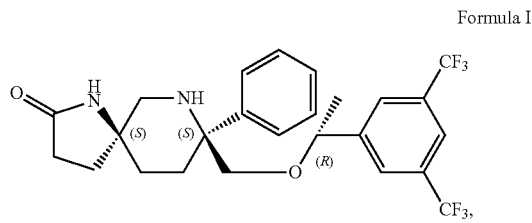

Formula I characterized by an x-ray powder diffraction pattern substantially as shown in FIG. 1.

11. The method of claim 4, wherein the one or more additional therapeutic agents are selected from a 5HT$_3$ inhibitor and a corticosteroid.

12. The method of claim 11, wherein the 5HT$_3$ inhibitor is selected from ondensetron, granisetron, palonosetron, dolasetron and tropisetron.

13. The method of claim 11, wherein the corticosteroid is dexamethasone.

14. The method of claim 5, wherein the medicament is administered contemporaneously with the chemotherapeutic agent such that the medicament is administered before administration of the chemotherapeutic agent.

15. The method according to claim 5, wherein the medicament is administered contemporaneously with the chemotherapeutic agent such that the medicament is administered during administration of the chemotherapeutic agent.

16. The method according to claim 5, wherein the medicament is administered contemporaneously with the chemotherapeutic agent such that the medicament is administered after administration of the chemotherapeutic agent.

* * * * *